(12) United States Patent
Baumert et al.

(10) Patent No.: US 8,759,010 B2
(45) Date of Patent: Jun. 24, 2014

(54) HOST CELL KINASES AS TARGETS FOR ANTIVIRAL THERAPIES AGAINST HCV INFECTION

(75) Inventors: Thomas Baumert, Strasbourg (FR); Joachim Lupberger, Strasbourg (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 81 days.

(21) Appl. No.: 13/120,368

(22) PCT Filed: Sep. 18, 2009

(86) PCT No.: PCT/EP2009/062095
§ 371 (c)(1), (2), (4) Date: Jun. 13, 2011

(87) PCT Pub. No.: WO2010/034670
PCT Pub. Date: Apr. 1, 2010

(65) Prior Publication Data
US 2011/0229484 A1 Sep. 22, 2011

(30) Foreign Application Priority Data
Sep. 26, 2008 (EP) .................................... 08305604

(51) Int. Cl.
*G01N 33/53* (2006.01)
(52) U.S. Cl.
USPC ........................................................ 435/7.1
(58) Field of Classification Search
USPC ........................................................ 435/7.1
See application file for complete search history.

(56) References Cited

U.S. PATENT DOCUMENTS

| | | | |
|---|---|---|---|
| 2006/0073127 A1 | 4/2006 | Kowalik et al. | |
| 2006/0275260 A1 | 12/2006 | Riviere et al. | |
| 2008/0081791 A1 | 4/2008 | Huang et al. | |

FOREIGN PATENT DOCUMENTS

| | | |
|---|---|---|
| WO | 2005/117885 | 12/2005 |
| WO | 2006/002422 | 1/2006 |
| WO | 2006/067175 | 6/2006 |
| WO | 2007/041362 | 4/2007 |
| WO | 2007/044894 | 4/2007 |
| WO | 2007/051862 | 5/2007 |
| WO | 2008/033466 | 3/2008 |
| WO | 2008/070117 | 6/2008 |

OTHER PUBLICATIONS

Wood et al. 2004; A unique structure for epidermal growth factor receptor bound to GW572016 (Iapatinib): Relationships among protein conformation, inhibitor off-rate, and receptor activity in tumor cells. Cancer Research 64(18): 6652-6659.*
International Search Report and Written Opinion in PCT/EP09/62095, dated Oct. 5, 2010.
Davies et al., Mutations of the BRAF gene in human cancer, Nature, Jun. 27, 2002, pp. 949-954, vol. 417.
Kainulainen et al., A Natural ErbB4 Isoform That Does Not Activate Phosphoinositide 3-Kinase Mediates Profileration but Not Survival or Chemotaxis, The Journal of Biological Chemistry, Mar. 24, 2000, pp. 8641-8649, vol. 275, No. 12.
Karaman, et al., A quantitative analysis of kinase inhibitor selectivity, Nature Biotechnology 26, 127-132, Jan. 8, 2008, 29 pp.
Lupberger et al., EGFR and EphA2 are host factors for hepatitis C virus entry and possible targets for antiviral therapy, Nature Medicine, Apr. 24, 2011, pp. 1-8.
Lupberger et al., EGFR and EphA2 are host factors for hepatitis C virus entry and possible targets for antiviral therapy, Nature Medicine (Supplement), Apr. 24, 2011, pp. 1-30.
Miura et al., Involvement of EphA2-mediated tyrosine phosphorylation of Shp2 in Shp2-regulated activation of extracellular signal-regulated kinase, Oncogene, 2013, pp. 1-10.
Schulze, et al., Phosphotyrosine interactome of the ErbB-receptor kinase family, Molecular Systems Biology, 2005, pp. 1-13.
Vindis et al., EphB1 recruits c-Src and p52 sch to activate MAPK/ERK and promote chemotaxis, The Journal of Cell Biology, Aug. 18, 2003, pp. 661-671, vol. 162, No. 4.
Wu et al., FGF19-induced Hepatocyte Proliferation Is Mediated through FGFR4 Activation, The Journal of Biological Chemistry, Feb. 19, 2010, pp. 5165-5170, vol. 285, No. 8.
Zona et al, HRas Signal Transduction Promotes Hepatitis C Virus Cell Entry by Triggering Assembly of the Host Tetraspanin Receptor Complex, Cell Host & Microbe 13, Mar. 13, 2013, pp. 302-313.

* cited by examiner

*Primary Examiner* — Karen Cochrane Carlson
(74) *Attorney, Agent, or Firm* — McAndrews, Held & Malloy Ltd.

(57) ABSTRACT

The present invention provides several networks of cellular protein kinases as potential targets for medical intervention against hepatitis C virus (HCV) infection and HCV-related diseases and disorders in mammals, including humans. The invention relates to therapeutic protocols and pharmaceutical compositions designed to inhibit the activity of one or more of these protein kinases for the prevention and/or treatment of infections and diseases caused by HCV. The invention also relates to methods for the identification of kinase inhibitors that may be used to treat and/or prevent HCV infections and HCV-related diseases.

4 Claims, 12 Drawing Sheets

|    | Protein Kinase | GenBank Accession Number of Corresponding Gene | Full Name |
|----|----------------|------------------------------------------------|-----------|
| 1  | FGR     | NM_005248 | Gardner-Rasheed feline sarcoma viral (v-fgr) oncogene homolog |
| 2  | CHUK    | NM_001278 | conserved helix-loop-helix ubiquitous kinase |
| 3  | PSKH1   | NM_006742 | protein serine kinase H1 |
| 4  | DGKB    | NM_004080 | diacylglycerol kinase, beta 90kDa |
| 5  | ILK     | NM_004517 | integrin-linked kinase |
| 6  | CKS1B   | NM_001826 | CDC28 protein kinase regulatory subunit 1B |
| 7  | PLK3    | NM_004073 | polo-like kinase 3 (Drosophila) |
| 8  | GKAP1   | NM_025211 | G kinase anchoring protein 1 |
| 9  | CALM2   | NM_001743 | calmodulin 2 (phosphorylase kinase, delta) |
| 10 | RPS6KA5 | NM_004755 | ribosomal protein S6 kinase, 90kDa, polypeptide 5 |
| 11 | MAGI1   | NM_173515 | membrane associated guanylate kinase interacting protein-like 1 |
| 12 | LTK     | NM_002344 | leukocyte tyrosine kinase |
| 13 | ITPKA   | NM_002220 | inositol 1,4,5-trisphosphate 3-kinase A |
| 14 | PIP5K2A | NM_005028 | phosphatidylinositol-4-phosphate 5-kinase, type II, alpha |
| 15 | ADK     | NM_001123 | adenosine kinase |
| 16 | STK11   | NM_000455 | serine/threonine kinase 11 (Peutz-Jeghers syndrome) |
| 17 | CDKN1B  | NM_004064 | cyclin-dependent kinase inhibitor 1B (p27, Kip1) |
| 18 | CHKB    | NM_005198 | choline kinase beta |
| 19 | BUB1B   | NM_001211 | BUB1 budding uninhibited by benzimidazoles 1 homolog beta (yeast) |
| 20 | STK38   | NM_007271 | serine/threonine kinase 38 |
| 21 | TYK2    | NM_003331 | tyrosine kinase 2 |
| 22 | PRKCABP | NM_012407 | protein kinase C, alpha binding protein |
| 23 | EGFR    | NM_005228 | epidermal growth factor receptor (erythroblastic leukemia viral (v-erb-b) oncogene homolog, avian) |
| 24 | CSK     | NM_004383 | c-src tyrosine kinase |
| 25 | AK3     | NM_013410 | adenylate kinase 3 |
| 26 | FER     | NM_005246 | fer (fps/fes related) tyrosine kinase (phosphoprotein NCP94) |
| 27 | PRKD2   | NM_016457 | protein kinase D2 |
| 28 | CDKL3   | NM_016508 | cyclin-dependent kinase-like 3 |
| 29 | PDIK1L  | NM_152835 | PDLIM1 interacting kinase 1 like |
| 30 | CKMT1   | NM_020990 | creatine kinase, mitochondrial 1 (ubiquitous) |
| 31 | CDKN2C  | NM_001262 | cyclin-dependent kinase inhibitor 2C (p18, inhibits CDK4) |
| 32 | CDK2    | NM_001798 | cyclin-dependent kinase 2 |
| 33 | CAMK2G  | NM_001222 | calcium/calmodulin-dependent protein kinase (CaM kinase) II gamma |
| 34 | EPHB4   | NM_004444 | EPH receptor B4 |

Figure 1 (A)

|    | Protein Kinase | GenBank Accession Number of Corresponding Gene | Full Name |
|----|---|---|---|
| 35 | GAK | NM_005255 | cyclin G associated kinase |
| 36 | PACSIN2 | NM_007229 | protein kinase C and casein kinase substrate in neurons 2 |
| 37 | SGK2 | NM_016276 | serum/glucocorticoid regulated kinase 2 |
| 38 | DCAMKL1 | NM_004734 | doublecortin and CaM kinase-like 1 |
| 39 | MAP3K13 | NM_004721 | mitogen-activated protein kinase kinase kinase 13 |
| 40 | IRAK2 | NM_001570 | interleukin-1 receptor-associated kinase 2 |
| 41 | ARAF | NM_001654 | v-raf murine sarcoma 3611 viral oncogene homolog |
| 42 | PAK4 | NM_005884 | p21(CDKN1A)-activated kinase 4 |
| 43 | MAPK7 | NM_002749 | mitogen-activated protein kinase 7 |
| 44 | ATR | NM_001184 | ataxia telangiectasia and Rad3 related |
| 45 | SRC | NM_005417 | v-src sarcoma (Schmidt-Ruppin A-2) viral oncogene homolog (avian) |
| 46 | PTK2B | NM_173176 | PTK2B protein tyrosine kinase 2 beta |
| 47 | EPHB1 | NM_004441 | EPH receptor B1 |
| 48 | BCR | NM_004327 | breakpoint cluster region |
| 49 | EPHA2 | NM_004431 | EPH receptor A2 |
| 50 | PIP5K2B | NM_003559 | phosphatidylinositol-4-phosphate 5-kinase, type II, beta |
| 51 | CDK3 | NM_001258 | cyclin-dependent kinase 3 |
| 52 | STK24 | NM_003576 | serine/threonine kinase 24 (STE20 homolog, yeast) |
| 53 | MKNK2 | NM_017572 | MAP kinase interacting serine/threonine kinase 2 |
| 54 | PKMYT1 | NM_004203 | protein kinase, membrane associated tyrosine/threonine 1 |
| 55 | FES | NM_002005 | feline sarcoma oncogene |
| 56 | ACVR2B | NM_001106 | activin A receptor, type IIB |
| 57 | MAP2K1IP1 | NM_021970 | mitogen-activated protein kinase kinase 1 interacting protein 1 |
| 58 | APEG1 | NM_005876 | aortic preferentially expressed protein 1 |
| 59 | JAK1 | NM_002227 | Janus kinase 1 (a protein tyrosine kinase) |
| 60 | AURKB | NM_004217 | aurora kinase B |
| 61 | CHKA | NM_001277 | choline kinase alpha |
| 62 | PRKACG | NM_002732 | protein kinase, cAMP-dependent, catalytic, gamma |
| 63 | DDR2 | NM_006182 | discoidin domain receptor family, member 2 |
| 64 | PIK3C2A | NM_002645 | phosphoinositide-3-kinase, class 2, alpha polypeptide |
| 65 | ADRBK1 | NM_001619 | adrenergic, beta, receptor kinase 1 |
| 66 | CALM3 | NM_005184 | calmodulin 3 (phosphorylase kinase, delta) |
| 67 | FASTK | NM_006712 | FAST kinase |
| 68 | WEE1 | NM_003390 | WEE1 homolog (S. pombe) |
| 69 | JAK2 | NM_004972 | Janus kinase 2 (a protein tyrosine kinase) |

Figure 1 (B)

|    | Protein Kinase | GenBank Accession Number of Corresponding Gene | Full Name |
|----|----------------|----------------------------------------------|-----------|
| 1  | FN3K     | NM_022158 | fructosamine 3 kinase |
| 2  | CIB2     | NM_006383 | calcium and integrin binding family member 2 |
| 3  | BCKDK    | NM_005881 | branched chain ketoacid dehydrogenase kinase |
| 4  | NEK9     | NM_033116 | NIMA (never in mitosis gene a)- related kinase 9 |
| 5  | STK33    | NM_030906 | serine/threonine kinase 33 |
| 6  | BRAF     | NM_004333 | v-raf murine sarcoma viral oncogene homolog B1 |
| 7  | STK22C   | NM_052841 | serine/threonine kinase 22C (spermiogenesis associated) |
| 8  | PI4KII   | NM_018425 | phosphatidylinositol 4-kinase type II |
| 9  | RIOK1    | NM_031480 | RIO kinase 1 (yeast) |
| 10 | CKB      | NM_001823 | creatine kinase, brain |
| 11 | Sharpin  | NM_030974 | shank-interacting protein-like 1 |
| 12 | RPS6KL1  | NM_031464 | ribosomal protein S6 kinase-like 1 |
| 13 | FLT3LG   | BF688722  | fms-related tyrosine kinase 3 ligand |
| 14 | HIPK3    | NM_005734 | homeodomain interacting protein kinase 3 |
| 15 | CDC2     | NM_001786 | cell division cycle 2, G1 to S and G2 to M |
| 16 | ERBB4    | NM_005235 | v-erb-a erythroblastic leukemia viral oncogene homolog 4 (avian) |
| 17 | CDC2L1   | NM_033487 | cell division cycle 2-like 1 (PITSLRE proteins) |
| 18 | PANK3    | NM_024594 | pantothenate kinase 3 |
| 19 | SKIP     | XM_051221 | SPHK1 (sphingosine kinase type 1) interacting protein |
| 20 | MAP4K5   | NM_006575 | mitogen-activated protein kinase kinase kinase kinase 5 |
| 21 | ATM      | NM_000051 | ataxia telangiectasia mutated (includes complementation groups A, C and D) |
| 22 | CDK4     | NM_000075 | cyclin-dependent kinase 4 |
| 23 | KIAA1446 | NM_020836 | brain-enriched guanylate kinase-associated protein |
| 24 | BMP2K    | NM_017593 | BMP2 inducible kinase |
| 25 | BMX      | NM_001721 | BMX non-receptor tyrosine kinase |
| 26 | CDK8     | NM_001260 | cyclin-dependent kinase 8 |
| 27 | TNK2     | NM_005781 | tyrosine kinase, non-receptor, 2 |
| 28 | NEK4     | NM_003157 | NIMA (never in mitosis gene a)-related kinase 4 |
| 29 | EPHA3    | NM_005233 | EPH receptor A3 |
| 30 | FGFR4    | NM_002011 | fibroblast growth factor receptor 4 |
| 31 | MAP3K7IP1| NM_006116 | mitogen-activated protein kinase kinase kinase 7 interacting protein 1 |
| 32 | MAPKAP1  | NM_024117 | mitogen-activated protein kinase associated protein 1 |

Figure 2

|   | Protein Kinase | GenBank Accession Number of Corresponding Gene | Full Name |
|---|---|---|---|
| 1 | CALM2 | NM_001743 | calmodulin 2 (phosphorylase kinase, delta) |
| 2 | CSK | NM_004383 | c-src tyrosine kinase |
| 3 | MAGI1 | NM_173515 | membrane associated guanylate kinase interacting protein-like 1 |
| 4 | ADK | NM_001123 | adenosine kinase |
| 5 | CDK3 | NM_001258 | cyclin-dependent kinase 3 |
| 6 | CDKN1B | NM_004064 | cyclin-dependent kinase inhibitor 1B (p27, Kip1) |
| 7 | CDKN2C | NM_001262 | cyclin-dependent kinase inhibitor 2C (p18, inhibits CDK4) |
| 8 | EPHA2 | NM_004431 | EPH receptor A2 |
| 9 | EPHB4 | NM_004444 | EPH receptor B4 |
| 10 | FASTK | NM_006712 | FAST kinase |
| 11 | FGR | NM_005248 | Gardner-Rasheed feline sarcoma viral (v-fgr) oncogene homolog |
| 12 | ILK | NM_004517 | integrin-linked kinase |
| 13 | IRAK2 | NM_001570 | interleukin-1 receptor-associated kinase 2 |
| 14 | PACSIN2 | NM_007229 | protein kinase C and casein kinase substrate in neurons 2 |
| 15 | PDIK1L | NM_152835 | PDLIM1 interacting kinase 1 like |
| 16 | PIP5K2B | NM_003559 | phosphatidylinositol-4-phosphate 5-kinase, type II, beta |
| 17 | PKMYT1 | NM_004203 | protein kinase, membrane associated tyrosine/threonine 1 |
| 18 | PLK3 | NM_004073 | polo-like kinase 3 (Drosophila) |
| 19 | PRKD2 | NM_016457 | protein kinase D2 |
| 20 | STK24 | NM_003576 | serine/threonine kinase 24 (STE20 homolog, yeast) |
| 21 | WEE1 | NM_003390 | WEE1 homolog (S. pombe) |
| 22 | CDKL3 | NM_016508 | cyclin-dependent kinase-like 3 |
| 23 | ADRBK1 | NM_001619 | adrenergic, beta, receptor kinase 1 |
| 24 | CKS1B | NM_001826 | CDC28 protein kinase regulatory subunit 1B |
| 25 | DCAMKL1 | NM_004734 | doublecortin and CaM kinase-like 1 |
| 26 | DDR2 | NM_006182 | discoidin domain receptor family, member 2 |
| 27 | EPS8L1 | NM_017729 | EPS8-like 1 |
| 28 | GAK | NM_005255 | cyclin G associated kinase |
| 29 | ITPKA | NM_002220 | inositol 1,4,5-trisphosphate 3-kinase A |
| 30 | MAPK7 | NM_002749 | mitogen-activated protein kinase 7 |
| 31 | PAK4 | NM_005884 | p21(CDKN1A)-activated kinase 4 |
| 32 | STK11 | NM_000455 | serine/threonine kinase 11 (Peutz-Jeghers syndrome) |
| 33 | STK38 | NM_007271 | serine/threonine kinase 38 |
| 34 | TYK2 | NM_003331 | tyrosine kinase 2 |

Figure 5 (A)

| | Protein Kinase | GenBank Accession Number of Corresponding Gene | Full Name |
|---|---|---|---|
| 35 | ACVR2B | NM_001106 | activin A receptor, type IIB |
| 36 | APEG1 | NM_005876 | aortic preferentially expressed protein 1 |
| 37 | ATM | NM_000051 | ataxia telangiectasia mutated |
| 38 | AURKB | NM_004217 | aurora kinase B |
| 39 | BMX | NM_001721 | BMX non-receptor tyrosine kinase |
| 40 | BRAF | NM_004333 | v-raf murine sarcoma viral oncogene homolog B1 |
| 41 | CDC2 | NM_001786 | cell division cycle 2, G1 to S and G2 to M |
| 42 | CDC2L1 | NM_033487 | cell division cycle 2-like 1 (PITSLRE proteins) |
| 43 | CDK4 | NM_000075 | cyclin-dependent kinase 4 |
| 44 | CDK8 | NM_001260 | cyclin-dependent kinase 8 |
| 45 | CHKA | NM_001277 | choline kinase alpha |
| 46 | CHKB | NM_005198 | choline kinase beta |
| 47 | CIB2 | NM_006383 | calcium and integrin binding family member 2 |
| 48 | CKMT1 | NM_020990 | creatine kinase, mitochondrial 1 (ubiquitous) |
| 49 | DGKB | NM_004080 | diacylglycerol kinase, beta 90kDa |
| 50 | EGFR | NM_005228 | epidermal growth factor receptor |
| 51 | EPHA3 | NM_005233 | EPH receptor A3 |
| 52 | EPHB1 | NM_004441 | EPH receptor B1 |
| 53 | FER | NM_005246 | fer (fps/fes related) tyrosine kinase (phosphoprotein NCP94) |
| 54 | FGFR4 | NM_002011 | fibroblast growth factor receptor 4 |
| 55 | FLT3LG | BF688722 | fms-related tyrosine kinase 3 ligand |
| 56 | FN3K | NM_022158 | fructosamine 3 kinase |
| 57 | GCK | NM_000162 | glucokinase (hexokinase 4, maturity onset diabetes of the young 2) |
| 58 | GKAP1 | NM_025211 | G kinase anchoring protein 1 |
| 59 | GRK4 | NM_182982 | G protein-coupled receptor kinase 4 |
| 60 | IKBKB | NM_001556 | inhibitor of kappa light polypeptide gene enhancer, kinase beta |
| 61 | MAP3K7IP1 | NM_006116 | mitogen-activated protein kinase 7 interacting protein 1 |
| 62 | MAPKAP1 | NM_024117 | mitogen-activated protein kinase associated protein 1 |
| 63 | NEK9 | NM_033116 | NIMA (never in mitosis gene a)- related kinase 9 |
| 64 | PANK3 | NM_024594 | pantothenate kinase 3 |
| 65 | PI4KII | NM_018425 | phosphatidylinositol 4-kinase type II |
| 66 | PIP5K2A | NM_005028 | phosphatidylinositol-4-phosphate 5-kinase, type II, alpha |
| 67 | PRKAG2 | NM_016203 | protein kinase, AMP-activated, gamma 2 non-catalytic subunit |
| 68 | PSKH1 | NM_006742 | protein serine kinase H1 |
| 69 | PTK2 | NM_173176 | PTK2 protein tyrosine kinase 2 |
| 70 | PTK2B | NM_173176 | PTK2B protein tyrosine kinase 2 beta |
| 71 | RIOK1 | NM_031480 | RIO kinase 1 (yeast) |
| 72 | RPS6KA5 | NM_004755 | ribosomal protein S6 kinase, 90kDa, polypeptide 5 |
| 73 | RPS6KL1 | NM_031464 | ribosomal protein S6 kinase-like 1 |
| 74 | Sharpin | NM_030974 | shank-interacting protein-like 1 |
| 75 | SKIP | XM_051221 | SPHK1 (sphingosine kinase type 1) interacting protein |
| 76 | STK22C | NM_052841 | serine/threonine kinase 22C (spermiogenesis associated) |
| 77 | TNK2 | NM_005781 | tyrosine kinase, non-receptor, 2 |
| 78 | ULK2 | NM_014683 | unc-51-like kinase 2 (C. elegans) |

Figure 5 (B)

HOST CELL KINASES AS TARGETS FOR ANTIVIRAL THERAPIES AGAINST HCV INFECTION

RELATED APPLICATIONS

The present application is filed pursuant to 35 U.S.C. 371 as a U.S. National Phase application of International Patent Application No. PCT/EP09/62095, which was filed Sep. 18, 2009, claiming the benefit of priority to European Patent Application No. EP 08 305 604.4 filed on Sep. 26, 2008. The entire text of the aforementioned applications is incorporated herein by reference in its entirety.

BACKGROUND OF THE INVENTION

Hepatitis C virus (HCV) is a major global health problem, with an estimated 150-200 million people infected worldwide, including at least 5 million infected individuals within the European Union (Pawlotsky, 2004). According to the World Health Organization, 3 to 4 million new infections occur each year. The infection is often asymptomatic. However, the majority of HCV-infected individuals develop chronic infection (Hoofnagle, 2002; Lauer, 2001; and Seeff, 1995). Chronic HCV infection frequently results in serious liver disease, including fibrosis and steatosis (Chisari, 2005). About 20% of patients with chronic HCV infection develop liver cirrhosis, which progresses to hepatocellular carcinoma in 5% of the cases (Hoofnagle, 2002).

Chronic HCV infection is the leading indication for liver transplantations (Seeff, 2002). Unfortunately, liver transplantation is not a cure for hepatitis C; viral recurrence is an invariable problem and leading cause of graft loss (Brown, 2005). No vaccine protecting against HCV is available. Current therapies include administration of ribavirin and/or interferon-alpha (IFN-α), two non-specific anti-viral agents. Using a combination treatment of pegylated IFN-α and ribavirin, persistent clearance is achieved in about 50% to 80% of patients with chronic hepatitis C. However, a large number of patients have contraindications to one of the components of the combination, cannot tolerate the treatment, do not respond to IFN therapy at all or experience a relapse when administration is stopped. In addition to limited efficacy and substantial side effects such as neutropenia, haemolytic anemia and severe depression, current antiviral therapies are also characterized by high cost.

Until recently, the development of more effective therapeutics to combat HCV infection has been hampered by the lack of a cell culture system supporting HCV replication. Robust production of infectious HCV in cell culture has now been achieved using a unique HCV genome derived from the blood of a Japanese patient with fulminant hepatitis C (JFH-1) (Wakita, 2005; Lindenbach, 2005; Zhong, 2005). The ability of the JFH-1 strain of HCV to release infectious particles in cell culture (HCVcc) and the development of retroviral HCV pseudoparticles (HCVpp) (Bartosch, 2003; Hsu, 2003) have allowed the complete viral life cycle to be explored. This, in turn, has led to the development of new antiviral agents targeting HCV protein processing and replication. However, many of these agents have proved to be toxic and highly susceptible to the development of viral resistance, suggesting that a different strategy is needed for the treatment of HCV infection.

HCV is a positive strand RNA virus classified in the *Hepacivirus* genus, within the Flaviviridae family. Translation of the major open reading frame of the HCV genome results in the production of an approximately 3000 amino acid long polyprotein, which is cleaved co- and post-translationally by the coordinated action of cellular and viral proteases into at least 10 mature proteins, including two envelope glycoproteins (E1 and E2). HCV initiates infection by attaching to molecules or receptors on the surface of hepatocytes. Since HCV entry is the first step of virus-host interactions, it represents a promising target for antiviral therapies. Several cell surface molecules have been identified that interact with HCV during viral binding and entry. These include the tetraspanin CD81 (Pileri, 1998), the scavenger receptor class B type I (SB-RI) (BScarselli, 2002), the tight junction proteins Claudin-1 (CLDN1) (Evans, 2007) and Occludin (Ploss, 2009), highly sulphated heparin sulphate (Barth, 2003), and the low-density lipoprotein (LDL) receptor (for review, see Barth, 2006 and Zeisel, 2008). All of these factors are expressed in many tissues and are not liver-specific. Although over-expression of CD81, SR-BI and tight junction proteins can confer HCV susceptibility to certain cell lines, other cell lines expressing the identified entry factors remain non-permissive. These findings suggest the presence of other co-entry factors mediating or modulating HCV entry.

Viruses are known to utilize signalling pathways of their target cells to their advantage during one or more steps of their life cycling including entry, internalization, replication and release (Cirone, 1990; Constantinescu, 1991; Pelkmans, 2005; Root, 2000; and Sieckarski, 2003). In recent years, it has become clear that the formation exchange between incoming viruses and the host cell during the first steps of virus-host interaction is not limited to the cues given to the virus by the cell resulting in cellular binding and entry of the virus. For many viruses, virus-host interaction resembles a two-way dialogue in which the virus takes advantage of the cell's own signal transduction systems to transmit signals to the cells (Smith, 2004). These signals—usually generated at the cell surface—induce changes that facilitate entry, prepare the cells for invasion and neutralize host defenses. Using a genomic analysis of responses to HCV envelop glycoproteins binding to hepatoma cells, the laboratory of the Applicants had previously demonstrated that binding of HCV envelop glycoproteins to host cells results in a cascade of intracellular signals modulating cellular gene expression, which may condition the cell for support of viral propagation (Fang, 2006).

SUMMARY OF THE INVENTION

The present invention is directed to novel targets for the medical intervention against hepatitis C virus (HCV) infections and HCV-related diseases in mammals, in particular humans. The invention provides the identity of human cellular protein kinases that can be used as targets of novel therapeutic protocols for the treatment and/or prevention of infections and diseases caused by HCV and for the identification and development of new HCV antiviral agents.

More specifically, with the aim of identifying novel HCV entry factors, the present Applicants have applied a functional siRNA (small interfering RNA) screen targeting 691 cellular kinases and associated proteins, and investigated the effects of kinase gene silencing on HCV entry using a model system based on HCV pseudotyped particles (HCVpp) (Bartosch, 2003). In certain experiments, to discriminate between HCV-specific and non-specific effects, they also studied the effect of kinase gene silencing on the infection of vesicular stomatitis virus pseudoparticles (VSVpp) (Barth, 2006) in side-by-side experiments. A preliminary experiment (see Example 1) led to the identification of 101 protein kinases for which the silencing of the corresponding genes resulted in a significant reduction of HCV entry into the cell. Among them were 69 protein kinases for which gene silencing led to a HCV-specific reduction of viral entry into cells without affecting VSVpp entry (see FIG. 1), and 32 protein kinases for which the silencing of the corresponding genes resulted in a marked reduction of HCV viral entry into cells with no regard to changes caused by gene silencing to VSVpp entry (see FIG. 2).

A second set of experiments (see Example 2) led to the identification of 78 human kinases with impact on HCV entry and initiation of HCV infection (see FIG. 5). These 78 human kinases are: CALM2, CSK, MAGI1, ADK, CDK3, CDKN1B, CDKN2C, EPHA2, EPHB4, FASTK, FGR, ILK, IRAK2, PACSIN2, PDIK1L, PIP5K2B, PKMYT1, PLK3, PRKD2, STK24, WEE1, CDKL3, ADRBK1, CKS1B, DCAMKL1, DDR2, EPS8L1, GAK, ITPKA, MAPK7, PAK4, STK11, STK38, TYK2, ACVR2B, APEG1, ATM, AURKB, BMX, BRAF, CDC2, CDC2L1, CDK4, CDK8, CHKA, CHKB, CIB2, CKMT1, DGKB, EGFR, EPHA3, EPHB1, FER, FGFR4, FLT3LG, FN3K, GCK, GKAP1, GRK4, IKBKB, MAP3K7IP1, MAPKAP1, NEK9, PANK3, PI4KII, PIP5K2A, PRKAG2, PSKH1, PTK2, PTK2B, RIOK1, RPS6KA5, RPS6KL1, Sharpin, SKIP, STK22C, TNK2, and ULK2 (the full name of these kinases and GenBank Accession numbers of the corresponding genes are presented in FIG. 5).

Of the 78 human kinases above, 34 were found to have a functional impact on HCVpp entry and HCVcc infection but no effect on VSV entry (see FIG. 5A and Example 2 for experimental details). These 34 human kinases are: CALM2, CSK, MAGI1, ADK, CDK3, CDKN1B, CDKN2C, EPHA2, EPHB4, FASTK, FGR, ILK, IRAK2, PACSIN2, PDIK1L, PIP5K2B, PKMYT1, PLK3, PRKD2, STK24, WEE1, CDKL3, ADRBK1, CKS1B, DCAMKL1, DDR2, EPS8L1, GAK, ITPKA, MAPK7, PAK4, STK11, STK38, and TYK2 (the full name of these kinases and GenBank Accession numbers of the corresponding genes are presented in FIG. 5A).

Bioinformatic analysis of the 78 human kinases using the STRING database revealed kinase networks regulating cell morphology including cell polarity, tight junction permeability and integrin signalling as well as networks of kinases involved in the cell cycle (FIG. 6C). A total of 23 human kinases were thus identified, including, in particular, 2 kinases that regulate cell polarity: STK11 and PRKAG2; 3 kinases that regulate tight junction: MAGI-1, EphA2 and EGFR; 4 kinases involved in integrin signaling: CSK, PTK2, PTK2B and ILK; and 8 kinases that are involved in the cell cycle: CDC2, CDK3, CDK4, CHKA, CDKN1B, CDKN2C, PKMYT1 and WEE1.

The Applicant then used cell culture derived infectious HCV (HCVcc) (Wakita, 2005) to verify the relevance of identified candidate kinases for the viral life cycle and to evaluate the potential of already approved kinase-inhibiting drugs for anti-HCV treatment. Human kinases that have been validated using this method include: STK11, PRKAG2, EPHA2, EGFR, and cyclin-dependent kinases (i.e., one or more of CDC2, CDK3, CDK4, CHKA, CDKN1B and CDKN2C).

All the identified cellular protein kinases represent potential targets for novel antiviral intervention. Accordingly, in one aspect the present invention provides these protein kinases as targets for antiviral therapies against HCV infection and HCV-related diseases.

In another aspect the present invention provides methods for the identification of compounds useful for the prevention and/or treatment of HCV infections and/or HCV-related diseases. Specifically, these methods involve contacting a biological system (e.g., a cell) that expresses or can express at least one protein kinase disclosed herein with a candidate compound and determining the activity of said protein kinase or a factor that is representative of the activity of said kinase. A candidate compound is identified as a potential HCV anti-viral agent (i.e., a compound potentially useful for treating and/or preventing infections or diseases caused by HCV) if the activity of the protein kinase is lower in the presence of the candidate compound than in the absence of the candidate compound. Alternatively, a candidate compound is identified as a potential HCV anti-viral agent if the factor representative of the activity of the kinase is different (lower or higher depending on the relationship between the factor and the activity) in the presence of the candidate compound and in the absence of the candidate compound.

In certain embodiments, the methods of the invention are used to screen individual candidate compounds. In other embodiments, the methods of the invention are used to screen libraries of candidate compounds. A candidate compound may belong to any of a wide variety of family of molecules. In certain embodiments, the candidate compound is selected from the group consisting of small molecules, monoclonal antibodies, polyclonal antibodies, RNA polymerase inhibitors, antisense compounds, ribozymes, siRNAs, siDNAs, and any combination thereof.

Any potential HCV anti-viral agent identified by a screening method described herein is encompassed by the present invention. In particular, the invention provides agents for preventing HCV infection of a cell, wherein the agents inhibit the activity of at least one protein kinase disclosed herein thereby preventing, blocking or inhibiting HCV entry into the cell. The invention also provides agents for preventing or treating HCV infection or a HCV-related disease in a subject, wherein the agents inhibit the activity of at least one protein kinase disclosed herein thereby preventing, blocking or inhibiting HCV entry into susceptible cells of the subject. The invention further provides agents for preventing HCV recurrence in a liver transplantation patient, wherein the agents inhibit the activity of at least one protein kinase disclosed herein thereby preventing, blocking or inhibiting HCV entry into susceptible cells of the patient. These agents (or kinase inhibitors) can be small molecules, monoclonal antibodies, polyclonal antibodies, RNA polymerase inhibitors, antisense compounds, siRNAs, siDNAs, ribozymes, and the like. In certain embodiments, these agents are compounds already known in the art to inhibit the activity of at least one of the protein kinases disclosed herein. Compounds already known in the art to inhibit the activity of at least one protein kinase include methyl-2-cyano-3,12-dioxoolean-1,9-dien-28-oate, cetuximab, AEE 788, panitumumab, BMS-599626, ARRY-334543, XL647, canertinib, gefitinib, HKI-272, PD 153035, lapatinib, vandetanib, erlotinib, BMS-387032, flavopiridol, XL647, dasatinib, AZM-475271, imatinib, AZD-1152, sorafenib, PD-0332991, derivatives thereof, physiologically acceptable salts thereof, and any combination thereof.

The present invention also relates to targeted systems and strategies for the prevention and/or treatment of HCV infection and HCV-related diseases. In particular, the present invention is directed to agents that interfere with HCV-host cells interactions, in particular, HCV entry, by inhibiting the activity of a kinase disclosed herein. These kinase inhibitors can be used in the prophylactic or therapeutic treatment of HCV infection (acute or chronic HCV infection) and HCV-related diseases or disorders (e.g., liver inflammation, cirrhosis, and hepatocellular carcinoma). Kinase inhibitors such as those provided herein that inhibit HCV entry into cells are particularly attractive as antiviral therapeutics.

The kinase inhibitors of the present invention can find application in a variety of prophylactic and therapeutic treatments. Accordingly, in another aspect, the inventive kinase inhibitors are provided for preventing HCV infection of a cell (e.g., a susceptible cell or a population of susceptible cells); for preventing or treating HCV infection or a HCV-related disease in a subject; and for preventing HCV recurrence in a liver transplantation patient.

In a related aspect, the present invention provides a method of reducing the likelihood of a susceptible cell of becoming infected with HCV as a result of contact with HCV, which comprises contacting the susceptible cell with an effective amount of an inventive kinase inhibitor. Also provided is a method of reducing the likelihood of a subject's susceptible cells of becoming infected with HCV as a result of contact with HCV, which comprises administering to the subject an effective amount of an inventive kinase inhibitor. The present invention also provides a method of treating or preventing HCV infection or a HCV-associated disease (e.g., a liver disease or pathology) in a subject in need thereof which comprises administering to the subject an effective amount of an inventive kinase inhibitor. Also provided is a method of preventing HCV recurrence in a liver transplantation patient, which comprises administering to the patient an effective amount of an inventive kinase inhibitor. Administration of an inventive kinase inhibitor to a subject may be by any suitable route, including, for example, parenteral, aerosol, oral and topical routes. The inventive kinase inhibitor may be administered alone or in combination with a therapeutic agent, such as an anti-viral agent.

Thus, kinase inhibitors of the invention include those agents that are already known in the art to be inhibitors of the activity of at least one target kinase described herein and those agents that are identified by any one of the screening assays disclosed herein.

In particular, in one embodiment, the invention provides for the use of Dorsomorphin, Dasatinib, Erlotinib, Flavopiridol, Vandetanib, Gefitinib or Lapatinib for the prevention or treatment of HCV infection. In another embodiment, the invention provides for the use of Dasatinib or Erlotinib for preventing HCV recurrence in a liver transplantation patient.

Kinase inhibitors of the invention may be administered per se or as pharmaceutical compositions. Accordingly, in another aspect, the present invention provides for the use of an inventive kinase inhibitor for the manufacture of medicaments, pharmaceutical compositions, or pharmaceutical kits for the treatment and/or prevention of HCV infection and HCV-associated diseases.

In a related aspect, the present invention provides a pharmaceutical composition comprising an effective amount of an inventive kinase inhibitor and at least one pharmaceutically acceptable carrier or excipient. In certain embodiments, the pharmaceutical composition is adapted for administration in combination with an additional therapeutic agent, such as an antiviral agent. In other embodiments, the pharmaceutical composition further comprises an additional therapeutic agent, such as an antiviral agent. Antiviral agents suitable for use in methods and pharmaceutical compositions of the present invention include, but are not limited to, interferons (e.g., interferon-alpha, pegylated interferon-alpha), ribavirin, anti-HCV (monoclonal or polyclonal) antibodies, RNA polymerase inhibitors, protease inhibitors, IRES inhibitors, helicase inhibitors, antisense compounds, ribozymes, and any combination thereof.

These and other objects, advantages and features of the present invention will become apparent to those of ordinary skill in the art having read the following detailed description of the preferred embodiments.

BRIEF DESCRIPTION OF THE DRAWING

FIG. 1 is a table presenting 69 human protein kinases identified, in the preliminary experiments (see Example 1), as potential targets for antiviral therapies against HCV infection. If silenced using siRNA, the genes encoding these protein kinases showed a HCV specific effect on viral entry into the cells (i.e., a reduction of HCV infection using HCVpp but no similar effect on control pseudotypes VSVpp). The full name of each of the protein kinases and the GenBank Accession Number of the corresponding genes are also given in the table.

FIG. 2 is a table presenting the 32 protein kinases identified, in the preliminary experiments (see Example 1), as potential targets for antiviral therapies against HCV infection. If silenced using siRNA, the genes encoding these protein kinases showed a marked reduction of viral entry into the cells with no regard to changes caused by gene silencing to VSVpp entry. The full name of each of the protein kinases and the GenBank Accession Number of the corresponding genes are also given in the table.

FIG. 5 is a table presenting 78 human protein kinases identified, in the second set of experiments (see Example 2), as having an impact on HCV entry and initiation of HCV infection. The first 34 human protein kinases presented in the table were found to have a functional impact on HCVpp entry and HCVcc infection but no effect on VSV entry (FIG. 5A). The full name of each of the protein kinases and the GenBank Accession Number of the corresponding genes are also given in the table.

DEFINITIONS

Figure 3:
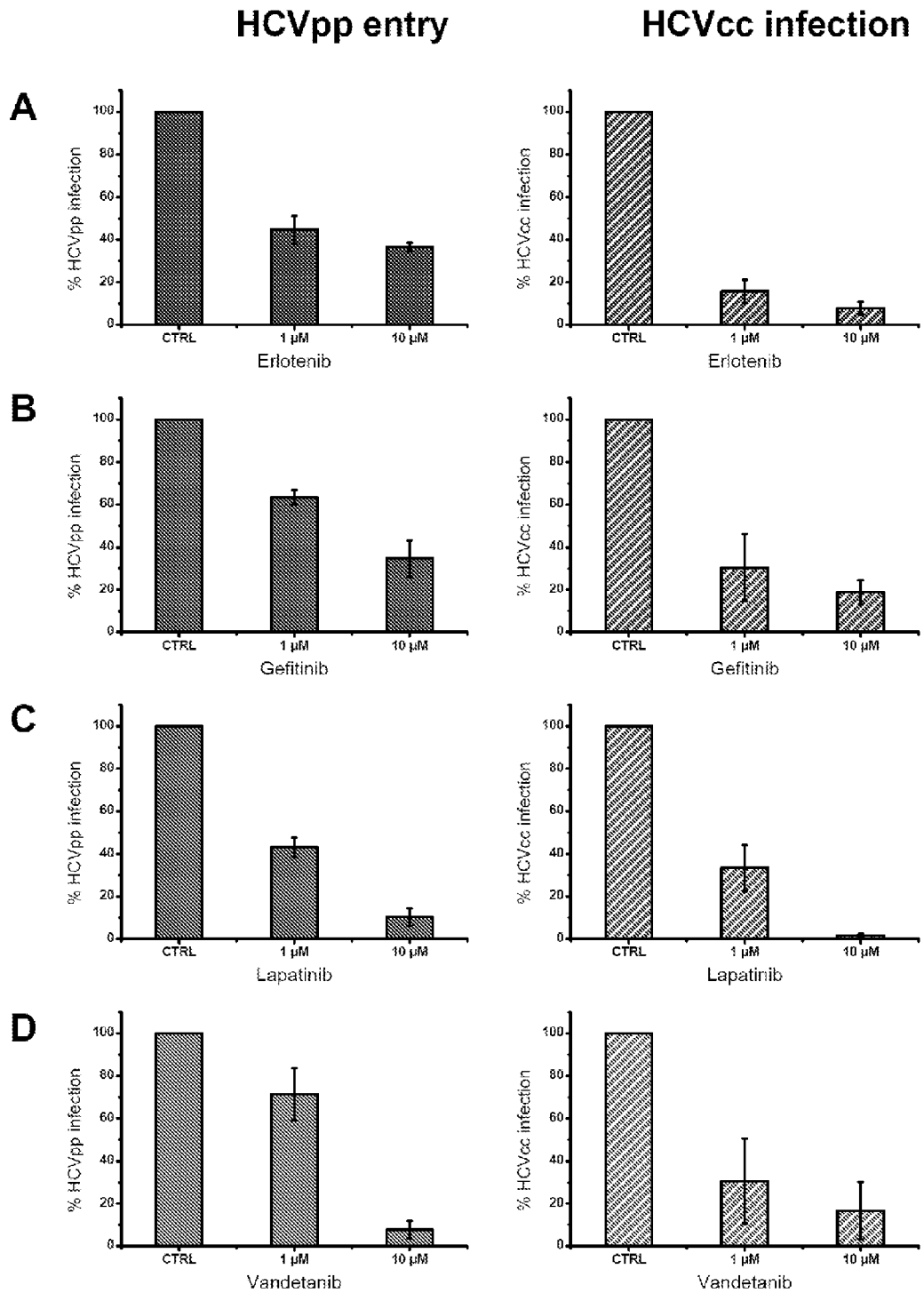
FIG. 3 demonstrates that inhibitors of epidermal growth factor receptor (EGFR) markedly inhibit HCVpp entry and HCVcc infection (see Example 1 for experimental details). Following incubation with Erlotenib (FIG. 3A), Gefitinib (FIG. 3B), Lapatinib (FIG. 3C) and Vandetanib (FIG. 3D) HCVpp entry (HCVpp H77C, genotype 1a) and HCVcc JFH1 infection were assessed by luciferase reporter gene expression or RT-PCR of HCV RNA in Huh7.5.1 cells. Cells were incubated 1 hours prior infection to 3 hours post-infection with solvent (CTRL), 1 µM or 10 µM of inhibitor. Luciferase activity was assessed 72 hours post-infection and normalized to the total protein content. Data are expressed as % HCVpp entry or HCVcc infection of control cells (CTRL=100%, mean±SD are shown).

Throughout the specification, several terms are employed that are defined in the following paragraphs.

The terms "kinase" and "protein kinase" are used herein interchangeably. They refer to an enzyme that catalyzes the transfer of a phosphate group from a nucleoside triphosphate to certain amino acid residues of another molecule (herein called "substrate" or "kinase substrate") that is involved in a signaling pathway. The phosphate group may be transferred, for example, from an ATP or GTP (adenosine or guanine triphosphate) molecule. Kinases may be transmembrane or intracellular proteins. Eukaryotic protein kinases are characterized by the sequence of a contiguous stretch of approximately 250 amino acids that constitutes the catalytic (kinase) domain. Kinases may be tyrosine kinases, serine/threonine kinases, histidine kinases, or dual-specificity kinases.

The terms "kinase activity" and "activity of a kinase" are used herein interchangeably and refer to the ability of a protein kinase to catalyze the phosphorylation of certain amino acid residues of a substrate molecule.

The term "inhibitor of kinase activity", when used in reference to a compound, refers to the ability of the compound to inhibit (e.g., fully suppress or partially decrease) the ability of a protein kinase to catalyze the transfer of a phosphate group from a nucleoside triphosphate to certain amino acid residues of a substrate molecule. In the practice of the present invention, inhibition of kinase activity may be achieved by any of a wide variety of mechanisms. However, irrespective of the mechanism, kinase activity inhibition results in the reduction of the ability of the kinase to catalyze the phosphorylation of its substrate(s). Thus, by "inhibition" is meant that the level of phosphorylation of the substrate is reduced at least 50% after incubation in the presence of the compound, for example in an assay of the invention. Preferably, the level of phosphorylation of the substrate is reduced at least 90% by the compound. More preferably, the level of phosphorylation of the substrate is reduced at least 95% by the compound. A candidate compound that induces such a decrease in the level of phosphorylation of a substrate molecule in a kinase assay of the invention is "identified" as an inhibitor of the activity of the kinase. Thus, in certain embodiments, an "inhibitor of kinase activity" is a compound that is/has been identified by a screening method of the invention as inhibiting/suppressing the activity of a given kinase.

The terms "protein kinase signaling pathway" and "protein kinase cascade" are used herein interchangeably. They refer to both the upstream and downstream components of the kinase protein signaling cascade.

The terms "substrate" and "kinase substrate" are used herein interchangeably. They refer to a molecule involved in one or more signaling pathways, which can become phosphorylated through the action of a kinase, and whose phosphorylation ultimately results in the modification of one or more cellular responses. Exemplary substrates include, but are not limited to, metabolic enzymes, gene regulatory proteins, cytoskeletal proteins or other protein kinases (e.g., downstream kinases that participate in the same signaling pathway).

The term "kinase activator", as used herein, refers to any extracellular or other type of stimulus that triggers activation of a kinase, which in turn induces phosphorylation of a substrate molecule. Examples of kinase activators include environmental stress signals (such as osmotic shock, heat shock, hypoxia, and UV radiation), chemical stress signals (such as oxidative stress, human carcinogens, and environmental pollutants), and biochemical stimuli (such as growth factors, cytokines, growth hormones, and neurotransmitters). Biochemical stimuli are generally molecules naturally secreted by cells that affect the function of other cells.

The term "constitutively active", when applied to a protein kinase, refers to a kinase that has the ability to catalyze substrate phosphorylation in the absence of a kinase activator. Constitutively active kinases may be endogenously expressed in cells used in an inventive screening assay or, alternatively, cells may be transformed to express a constitutively active kinase.

As used herein, the term "gene" refers to a polynucleotide that encodes a discrete product, be it a RNA or a protein, and may include regulatory sequences preceding (5' non-coding sequences) and following (3' non-encoding sequences) the coding sequence. As more than one polynucleotide may encode a discrete product, the term also includes alleles and polymorphisms of a gene that encode the same product, or a functionally associated (including gain, loss, or modulation of function) analog thereof.

As used herein, the term "substantially homogeneous population", when applied to cells, refers to a population of cells, wherein at least about 80% and preferably at least about 90% of the cells in the population are of the same cell type. Examples of cell types include, but are not limited to, platelets, lymphocytes, T-cells, B-cells, natural killer cells, endothelial cells, tumor cells, epithelial cells, granulocytes, monocytes, mast cells, neurocytes, and the like.

The terms "system" and "biological system" are used herein interchangeably. They refer to an in vitro, in vivo or ex vivo biological entity such as a cell, a biological fluid, or a biological tissue. A system may, for example, originate from a living subject (e.g., it may be obtained by biopsy or by drawing blood) or from a deceased subject (e.g., it may be obtained at autopsy). The subject from which a biological system is obtained may be an animal model for HCV infection. Alternatively, it may be a human.

As used herein, the term "subject" refers to a human or another mammal (e.g., primate, dog, cat, goat, horse, pig, mouse, rat, rabbit, and the like), that can be the host of Hepatitis C virus (HCV), but may or may not be infected with the virus, and may or may not suffer from a HCV-related disease. Non-human subjects may be transgenic or otherwise modified animals. In many embodiments of the present invention, the subject is a human being. In such embodiments, the subject is often referred to as an "individual". The term "individual" does not denote a particular age, and thus encompasses newborns, children, teenagers, and adults.

As used herein, the term "HCV" refers to any major HCV genotype, subtype, isolate and/or quasispecies. HCV genotypes include, but are not limited to, genotypes 1, 2, 3, 4, 5, and 6; HCV subtypes include, but are not limited to, subtypes 1a, 1b, 2a, 2b, 2c, 3a, 4a-f, 5a and 6a.

The terms "afflicted with HCV" and "infected with HCV" are used herein interchangeably. When used in reference to a subject, they refer to a subject that has at least one cell which is infected by HCV. The term "HCV infection" refers to the introduction of HCV genetic information into a target cell, such as by fusion of the target cell membrane with HCV or an HCV envelope glycoprotein-positive cell.

The terms "HCV-related disease" and "HCV-associated disease" are herein used interchangeably. They refer to any disease or disorder known or suspected to be associated with and/or directly or indirectly caused by HCV. HCV-related (or HCV-associated) diseases include, but are not limited to, a wide variety of liver diseases, such as subclinical carrier state of acute hepatitis, chronic hepatitis, cirrhosis, and hepatocellular carcinoma. The terms include symptoms and side effects of any HCV infection, including latent, persistent and subclinical infections, whether or not the infection is clinically apparent.

The term "treatment" is used herein to characterize a method or process that is aimed at (1) delaying or preventing the onset of a disease or condition (e.g., HCV infection or HCV-related disease); (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventing action. Alternatively or additionally, a treatment may be administered after initiation of the disease, for a therapeutic action.

A "pharmaceutical composition" is defined herein as comprising an effective amount of at least one biologically active ingredient (e.g., a protein kinase inhibitor) and at least one pharmaceutically acceptable carrier or excipient.

As used herein, the term "effective amount" refers to any amount of a compound or composition that is sufficient to fulfill its intended purpose(s), e.g., a desired biological or medicinal response in a cell, tissue, system or subject. For example, in certain embodiments of the present invention, the purpose(s) may be: to inhibit the activity of a kinase; to prevent HCV infection; to prevent the onset of a HCV-related disease; to slow down, alleviate or stop the progression, aggravation or deterioration of the symptoms of a HCV-related disease (e.g., chronic hepatitis C, cirrhosis, and the like); to bring about amelioration of the symptoms of the disease; and/or to cure the HCV-related disease.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18$^{th}$ Ed., 1990, Mack Publishing Co.: Easton, Pa., which is incorporated herein by reference in its entirety).

The terms "susceptible cell" and "HCV-susceptible cell" are used herein interchangeably. They refer to any cell that may be infected with HCV. Susceptible cells include, but are not limited to, liver or hepatic cells, primary cells, hepatoma cells, CaCo2 cells, dendritic cells, placental cells, endometrial cells, lymph node cells, lymphoid cells (B and T cells), peripheral blood mononuclear cells, and monocytes/macrophages.

The term "preventing, inhibiting or blocking HCV infection" when used in reference to an agent (e.g., a protein kinase inhibitor), means reducing the amount of HCV genetic information introduced into a susceptible cell or susceptible cell population as compared to the amount that would be introduced in the absence of the agent.

The term "candidate compound" refers to any naturally occurring or non-naturally occurring molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues to be tested for an activity of interest. In the screening methods of the invention, candidate compounds are evaluated for their ability to inhibit the activity of a given protein kinase.

The term "small molecule", as used herein, refers to any natural or synthetic organic or inorganic compound or factor with a low molecular weight. Preferred small molecules have molecular weights of more than 50 Daltons and less than 2,500 Daltons. More preferably, small molecules have molecular weights of less than 600-700 Daltons. Even more preferably, small molecules have molecular weights of less than 350 Daltons.

As used herein, the term "physiologically acceptable salts or prodrugs" refers to salts or prodrugs that are, within the scope of sound medical judgment, suitable for use in contact with the tissues of patients without undue toxicity, irritation, allergic response, and the like, commensurate with a reasonable benefit/risk ratio, and effective for their intended use.

The term "salts" refers to any acid addition or base addition salt that retains the biological activity and properties of the corresponding free base or free acid, respectively, and that is not biologically or otherwise undesirable. Acid addition salts are formed with inorganic acids (e.g., hydrochloric, hydrobromic, sulfuric, nitric, phosphoric acids, and the like); and organic acids (e.g., acetic, propionic, pyruvic, maleic, malonic, succinic, fumaric, tartaric, citric, benzoic, mandelic, methanesulfonic, ethanesulfonic, p-toluenesulfonic, salicylic acids, and the life). Base addition salts can be formed with inorganic bases (e.g., sodium, potassium, lithium, ammonium, calcium, magnesium, zinc, aluminum salts, and the like) and organic bases (e.g., salts of primary, secondary, and tertiary amines, substituted amines including naturally-occurring substituted amines, cyclic amines and basic ion exchange resins, such as isopropylamine, trimethylamine, diethylamine, triethylamine, tripropylamine, ethanolamine, 2-dimethyl-aminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like).

The term "prodrug" refers to a compound that, upon in vivo administration, is metabolized or otherwise converted to the biologically, pharmaceutically or therapeutically active form of the compound. The prodrug may be designed to alter the metabolic stability or the transport characteristics of a compound, to mask side effects or toxicity, to improve the flavor of a compound and/or to alter other characteristics or properties of a compound. By virtue of knowledge of pharmacodynamic processes and drug metabolisms in vivo, once a pharmaceutically active compound is identified, those of skill in the pharmaceutical art generally can design prodrugs of the compound (Nogrady, "*Medicinal Chemistry A Biochemical Approach*", 1985, Oxford University Press: N.Y., pages 388-392). Procedures for the selection and preparation of suitable prodrugs are also known in the art.

The terms "approximately" and "about", as used in reference to a number, generally include numbers that fall within a range of 10% in either direction of the number (greater than or less than the number) unless otherwise stated or otherwise evident from the context (except where such number would exceed 100% of a possible value).

DETAILED DESCRIPTION OF CERTAIN PREFERRED EMBODIMENTS

As mentioned above, the present invention provides a panel of new HCV entry factors as putative targets for antiviral substances which were identified by applying a functional siRNA screen targeting 691 cellular kinases and associated proteins and investigating the effects of kinase gene silencing on HCV entry. The identified protein kinases that directly or indirectly play a role in HCV entry and infection provide for, among other things, novel therapeutic protocols, useful antiviral therapeutics, and new screening methods (e.g., assays) and materials to find and develop new antiviral agents.

I—Host Cellular Protein Kinases

In their refined set of experiments (see Example 2 and FIG. 3), the Applicants have performed primary and secondary screens to identify human kinase genes with impact on HCV entry and initiation of HCV infection. More specifically, silencing of these genes resulted in a marked reduction in HCVpp and HCVcc entry into cells. These screens led to the identification of 78 kinase genes with the following GenBank Accession numbers: NM_001743, NM_004383, NM_173515, NM_001123, NM_001258, NM_004064, NM_001262, NM_004431, NM_004444, NM_006712, NM_005248, NM_004517, NM_001570, NM_007229, NM_152835, NM_003559, NM_004203, NM_004073, NM_016457, NM_003576, NM_003390, NM_016508, NM_001619, NM_001826, NM_004734, NM_006182, NM_017729, NM_005255, NM_002220, NM_002749, NM_005884, NM_000455, NM_007271, NM_003331, NM_001106, NM_005876, NM_000051, NM_004217, NM_001721, NM_004333, NM_001786, NM_033487, NM_000075, NM_001260, NM_001277, NM_005198, NM_006383, NM_020990, NM_004080, NM_005228, NM_005233, NM_004441, NM_005246, NM_002011, BF688722, NM_022158, NM_000162, NM_025211, NM_182982, NM_001556, NM_006116, NM_024117, NM_033116, NM_024594, NM_018425, NM_005028, NM_016203, NM_006742, NM_173176, NM_031480, NM_004755, NM_031464, NM_030974, XM_051221, NM_052841, NM_005781, and NM_014683.

Accordingly, the present invention provides 78 human cellular protein kinases as novel targets for medical intervention against HCV infection and HCV-related diseases. These protein kinases are encoded by the 78 genes mentioned above. More specifically, these kinases are: CALM2, CSK, MAGI1, ADK, CDK3, CDKN1B, CDKN2C, EPHA2, EPHB4, FASTK, FGR, ILK, IRAK2, PACSIN2, PDIK1L, PIP5K2B, PKMYT1, PLK3, PRKD2, STK24, WEE1, CDKL3, ADRBK1, CKS1B, DCAMKL1, DDR2, EPS8L1, GAK, ITPKA, MAPK7, PAK4, STK11, STK38, TYK2, ACVR2B, APEG1, ATM, AURKB, BMX, BRAF, CDC2, CDC2L1, CDK4, CDK8, CHKA, CHKB, CIB2, CKMT1, DGKB, EGFR, EPHA3, EPHB1, FER, FGFR4, FLT3LG, FN3K, GCK, GKAP1, GRK4, IKBKB, MAP3K7IP1, MAPKAP1, NEK9, PANK3, PI4KII, PIP5K2A, PRKAG2, PSKH1, PTK2, PTK2B, RIOK1, RPS6KA5, RPS6KL1, Sharpin, SKIP, STK22C, TNK2, and ULK2. The full names of the protein kinases (and corresponding genes) and the GenBank Accession numbers of the genes are provided in the table presented in FIG. 5.

A side-by-side screen was performed to identify kinase genes which, if silenced using siRNA, showed a marked reduction in HCVpp and HCVcc entry into cells but did not cause any changes in VSVpp entry into cells. This led to the identification of 34 kinase genes with the following GenBank Accession numbers: NM_001743, NM_004383, NM_173515, NM_001123, NM_001258, NM_004064, NM_001262, NM_004431, NM_004444, NM_006712, NM_005248, NM_004517, NM_001570, NM_007229, NM_152835, NM_003559, NM_004203, NM_004073, NM_016457, NM_003576, NM_003390, NM_016508, NM_001619, NM_001826, NM_004734, NM_006182, NM_017729, NM_005255, NM_002220, NM_002749, NM_005884, NM_000455, NM_007271, and NM_003331.

Accordingly, the present invention provides 34 human cellular protein kinases as novel targets for medical intervention against viral infection, in particular HCV infections and HCV-related diseases. These protein kinases are encoded by the 34 genes mentioned above. More specifically, these kinases are: CALM2, CSK, MAGI1, ADK, CDK3, CDKN1B, CDKN2C, EPHA2, EPHB4, FASTK, FGR, ILK, IRAK2, PACSIN2, PDIK1L, PIP5K2B, PKMYT1, PLK3, PRKD2, STK24, WEE1, CDKL3, ADRBK1, CKS1B, DCAMKL1, DDR2, EPS8L1, GAK, ITPKA, MAPK7, PAK4, STK11, STK38, and TYK2. The full names of the kinases (and corresponding genes) and the GenBank Accession numbers of the genes are provided in the table presented in FIG. 5A.

Figure 6:
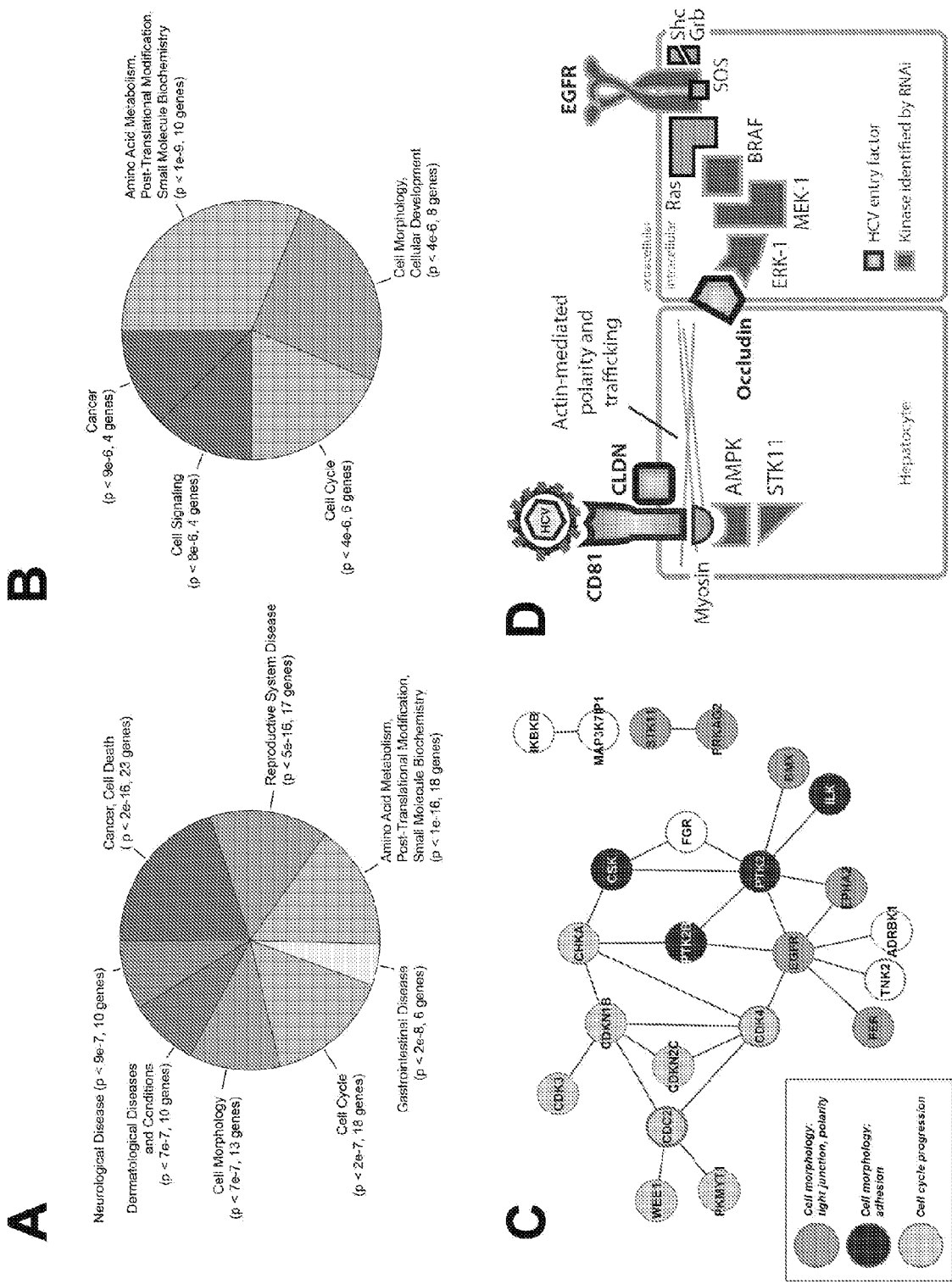
FIG. 6 shows the results of biological processes and protein association network analyses of the cellular kinases identified in the second set of experiments as having a marked impact on HCV entry. The 78 identified cellular kinases involved in HCV entry (A) and the 34 identified kinases with impact on HCV entry but not on VSV entry (B) were analyzed using the Ingenuity Pathways database. This analysis identified terms with the most prevalent biological processes associated with the identified candidate kinases within an organism (threshold p value<$10^{-5}$). The most significant terms of biological function were ordered by ascending p-values. (C) Protein association network of the 78 kinases involved in HCV entry identified by STRING analysis. Lines connecting kinases shown direct (physical) and indirect (functional) associations derived from numerous sources, including experimental repositories, computational prediction methods and public text collections. Kinases involved in the regulation of cell morphology, tight junctions and cell polarity (green), cell adhesion (dark green) and cell cycle progression (blue) are highlighted. (D) Model of the impact of cellular kinases identified in the RNAi screen on HCV entry mechanisms. HCV entry factors are depicted in orange, cellular kinases identified in the entry screen are depicted in red.

A bioinformatic analysis using the STRING database performed on the 78 human kinases revealed kinase networks regulating cell morphology including cell polarity, tight junction permeability and integrin signaling as well as networks of kinases involved in the cell cycle (FIG. 6 C). A total of 23 human kinases were thus identified, including, in particular, 2 kinases that regulate cell polarity; 3 kinases that regulate tight junction; 4 kinases that are involved in integrin signaling: and 8 kinases that are involved in the cell cycle.

Accordingly, the present invention provides 17 human cellular protein kinases as novel targets for medical intervention against viral infection, in particular HCV infections and HCV-related diseases. These 17 protein kinases are: STK11, PRKAG2, MAGI-1, EphA2, EGFR, CSK, PTK2, PTK2B, ILK, CDC2, CDK3, CDK4, CHKA, CDKN1B, CDKN2C, PKMYT1 and WEE1.

The Applicants have then used approved kinase-inhibiting drugs to validate the identified protein kinases as targets for medical intervention against HCV infection (see Examples 1 and 2). They found that preincubation of Huh7.5 cells with Dorsomorphin, an inhibitor of AMPK activity, markedly inhibited HCVpp entry, thus confirming the role of STK11 and PRKAG2. Similarly, preincubation with Dasatinib, an inhibitor of EphA2 function, markedly inhibited HCVpp entry in primary human hepatocytes and HCVcc infection of Huh7.5.1 cells, which confirmed that the EphA2 function is important for HCV entry. In addition, the Applicants found that inhibition of EGFR activity using Erlotinib dose-dependently inhibited HCV entry and HCV infection, thus confirming the role of EGFR. Similar results were obtained using other EGFR inhibitors such as Vandetanib, Gefitinib and Lapatinib). Finally, Flavopiridol, a well-characterized inhibitor of the CDK family, markedly inhibited HCVpp entry in primary human hepatocytes, confirming the role of cyclin-dependent kinases, in particular CDK3.

Accordingly, the present invention provides the following protein kinases as novel targets for medical intervention against viral infection, in particular HCV infections and HCV-related diseases. These protein kinases are: STK11, PRKAG2, EPHA2, EGFR, and cyclin-dependent kinases, in particular CDK3.

II—Kinase Inhibitors as HCV Anti-Viral Agents

The human cellular protein kinases identified by the present inventors can be used as targets for the identification, design and development of new HCV antiviral agents. A kinase inhibitor useful as a HCV antiviral agent may belong to any of a wide variety of families of molecules including, but not limited to, organic compounds (e.g., small molecules, saccharides, steroids, and the like), monoclonal or polyclonal antibodies (e.g., antibodies that bind to the kinase), peptides, polypeptides, nucleic acid molecules (e.g., antisense compounds, ribozymes, triple helix molecules, SELEX RNAs, and the like). As already mentioned above, a kinase inhibitor according to the invention may exert its effects by one or more of a variety of mechanisms that result in the inhibition (e.g., complete suppression or partial decrease) of the ability of the protein kinase of interest to catalyze the phosphorylation of its substrate. Thus, a kinase inhibitor may, for example, exert its effects by inhibiting, blocking or preventing the expression of the gene encoding the kinase of interest (gene therapy approach), and/or by inhibiting, blocking or preventing enzymatic activity (including through competition or modulation of the activity or function of a substrate of the kinase, or through competitive binding to the kinase or its catalytic/enzymatic domain, through competitive binding to the kinase substrate(s) and/or to any upstream and/or downstream kinase effectors).

The present invention provides methods to identify compounds useful for preventing and/or treating HCV infections by screening candidate compounds for their ability to inhibit the activity of at least one of the kinases disclosed herein (see below). The invention encompasses any of the compounds identified as a kinase inhibitor by a screening method of the invention. However, the present invention also encompasses the use of compounds that are already known in the art to inhibit the activity of at least one of the protein kinases disclosed herein. These protein kinase inhibitors are often designed as anti-cancer drugs and are developed by different companies including, but not limited to, Genetech, Boehringer Ingelheim, Imclone, Novartis, Roche, AstraZeneca, OSI, Onyx, Bayer, Pfizer, BMS, Sanofi, GSK and Amgen.

Examples of known kinase inhibitors include, but are not limited to, methyl 2-cyano-3,12-dioxoolean-1,9-dien-28-oate (for the inhibition of CHUK); cetuximab (for the inhibition of EGFR), AEE 788, panitumumab, BMS-599626, ARRY-334543, XL647, canertinib, gefitinib, HKI-272, PD 153035, lapatinib, vandetanib, and erlotinib (for the inhibition of EGFR); BMS-387032 and flavopiridol (for the inhibition of CDK2, CDK3, CDK4, and CDK8); XL647 (for the inhibition of EPHB4); dasatinib and AZM-475271 (for the inhibition of SRC); imatinib (for the inhibition of BCR); dasatinib (for the inhibition of EPHA2); and AZD-1152 (for the inhibition of AURKB). Other examples of known kinase inhibitors include, but are not limited to, sorafenib (for the inhibition of BRAF); BMS-599626 (for the inhibition of ERBB4); PD-0332991 and flavopiridol (for the inhibition of CDK4).

As mentioned above, the present Applicants have shown that known inhibitors of some of the kinases identified markedly inhibited HCV entry and HCV infection (see Examples 1 and 2). Accordingly, the present invention provides for the use of Erlotinib (Tarceva®), Vandetanib (Zactima®), Gefitinib (Iressa®) or Lapatinib (Tyverb®), all known inhibitors of EGFR activity, for the prevention and/or treatment of HCV infection. The invention also provides for the use of Dorsomorphin, an inhibitor of AMPK activity, of Dasatinib (Sprycel®), an inhibitor of EphA2 function, or of Flavopiridol (Alvocidib®), a well-characterized inhibitor of the CDK family including CDK3, CDC2, CDK2, CDK4, and CDK8, for the prevention and/or treatment of HCV infection.

The present Applicants have also shown that inhibition of EGFR and EphA2 function by Erlotinib and Dasatinib, respectively, blocked the entry of all major HCV genotypes and of a large panel of viral strains isolated from HVC-infection patients during liver transplantation (see Example 2). Accordingly, the present invention provides for the use of Erlotinib or Dasatinib for preventing HCV recurrence in a liver transplantation patient.

In a related aspect, the present invention provides for the use of anyone of these known kinase inhibitors for the manufacture of a medicament for the prevention or treatment of HCV infection and HCV-related diseases.

III—Methods of Identification of Kinase Inhibitors as HCV Anti-Viral Agents

As mentioned above, the present invention provides methods for the identification of compounds that reduce, inhibit or suppress HCV entry into cells and/or HCV infection by inhibiting the activity of at least one kinase of the invention. A variety of assay protocols and detection techniques are well known in the art and can easily be adapted for this purpose by one skilled in the art. Such methods include, but are not limited to, high-throughput assays (e.g., microarray technology, phage display technology) and in vitro and in vivo cellular and tissue assays.

In certain preferred embodiments, the methods of the present invention comprise incubating a biological system, which expresses (or can express) at least one kinase of the invention, with a candidate compound under conditions and for a time sufficient for the candidate compound to modulate the kinase activity; and measuring the activity of the kinase. Candidate compounds that decrease the activity of the kinase are identified as kinase inhibitors and potential HCV anti-viral agents. In certain embodiments, a method according to the invention more specifically includes incubating a biological system, which expresses (or can express) at least one kinase of the invention with a candidate compound under conditions and for a time sufficient for the candidate compound to modulate the activity of the kinase, thereby obtaining a test system; incubating the biological system under the same conditions and for the same time absent the candidate compound, thereby obtaining a control system; measuring in the test system, at least one factor that is representative of the activity of the kinase; measuring that factor in the control system; comparing the factor measured in the test system and the control system; and determining that the candidate compound inhibits the activity of the kinase if the factor measured in the test system is less than or greater than the factor measured in the control system.

The screening methods provided herein will lead to the discovery and development of HCV anti-viral agents that exert their effects by inhibiting the activity of one or more kinases of the invention. These agents may be potentially useful in the treatment and/or prevention of HCV infection and/or HCV-related diseases and conditions.

A. Biological Systems

The assays and screening methods of the present invention may be carried out using any type of biological systems, i.e., a cell, a biological fluid, a biological tissue, or an animal. In certain embodiments, the system is a biological entity that expresses (or can express) at least one kinase of the invention (e.g., a cell, a blood sample, a tissue sample, whole or part of an organ, e.g., the liver, or an animal model). In certain embodiments, the biological system may be infected with HCV (e.g., a HCV-susceptible cell).

In certain embodiments, the assay and screening methods of the present invention are carried out using cells that can be grown in standard tissue culture plastic ware. Such cells include all normal and transformed cells derived from any recognized sources. Preferably, cells are of mammalian (human or animal, such as rodent or simian) origin.

More preferably, cells are of human origin. Mammalian cells may be of any organ or tissue origin (e.g., brain, liver, lung, heart, kidney, skin, muscle, bone, bone marrow or blood, etc) and of any cell types. Suitable cell types include, but are not limited to, basal cells, epithelial cells, platelets, lymphocytes, T-cells, B-cells, natural killer cells, reticulocytes, granulocytes, monocytes, mast cells, neurocytes, neuroblasts, cytomegalic cells, dendritic cells, macrophages, endothelial cells, tumor cells, interstitial cells, Kupffer cells, Langerhans cells, littoral cells, tissue cells such as muscle cells and adipose cells, enucleated cells, and the like. In certain embodiments, assays and screening methods of the invention are performed using cells that are HCV-susceptible and that express at least one kinase of the invention. Examples of such cells include, but are not limited to, liver or hepatic cells, primary human hepatocytes, primary cells from human or other species, hepatoma cells, CaCo2 cells, dendritic cells, placental cells, endometrial cells, lymph node cells, lymphoid cells (B and T cells), peripheral blood mononuclear cells, and monocytes/macrophages.

Cells to be used in the practice of the assays and screening methods of the present invention may be primary cells, secondary cells, or immortalized cells (e.g., established cell lines). They may be prepared by techniques well known in the art (for example, cells may be obtained by drawing blood from or by biopsy of a patient or a healthy donor) or purchased from immunological and microbiological commercial resources (for example, from the American Type Culture Collection, Manassas, Va.). Alternatively or additionally, cells may be genetically engineered to contain, for example, a gene of interest such as a gene expressing a kinase of interest.

In certain embodiments, the cells used in the inventive screening methods are of more than one cell type. In other embodiments, the cells are of a single cell type. Preferably, cells are from a substantially homogeneous population of cells, wherein at least about 80% and preferably at least about 90% of the cells in the population are of the same cell type. Cells to be used in the methods of the invention may originate from different subjects or individuals of the same species. However, preferably, cells originate from a single subject or individual.

Selection of a particular cell type and/or cell line to perform an assay according to the present invention will be governed by several factors such as the nature of the kinase whose activity is under investigation and the intended purpose of the assay. For example, an assay developed for primary drug screening (i.e., first round(s) of screening) may preferably be performed using established cell lines, which are commercially available and usually relatively easy to grow, while an assay to be used later in the drug development process may preferably be performed using primary or secondary cells, which are often more difficult to obtain, maintain, and/or to grow than immortalized cells but which represent better experimental models for in vivo situations.

Examples of established cell lines that can be used in the practice of the assays and screening methods of the present invention include HepG2 liver hepatoma cells, Hep3B liver hepatoma cells, primary hepatocytes, Huh7-derived cell lines, and immortalized hepatocytes. Primary and secondary cells that can be used in the inventive screening methods include, but are not limited to, epithelial cells, platelets, lymphocytes, monocytes, myocytes, macrophages, hepatocytes, endothelial cells, and the like.

Cells to be used in the inventive assays may be cultured according to standard cell culture techniques. For example, cells are often grown in a suitable vessel in a sterile environment at 37° C. in an incubator containing a humidified 95% air-5% $CO_2$ atmosphere. Vessels may contain stirred or stationary cultures. Various cell culture media may be used including media containing undefined biological fluids such as fetal calf serum, as well as media which are fully defined, such as 293 SFM serum free medium (Invitrogen Corp., Carlsbad, Calif.). Cell culture techniques are well known in the art and established protocols are available for the culture of diverse cell types (see, for example, R. I. Freshney, "*Culture of Animal Cells: A Manual of Basic Technique*", $2^{nd}$ Edition, 1987, Alan R. Liss, Inc.).

In certain embodiments, the screening methods are performed using cells contained in a plurality of wells of a multi-well assay plate. Such assay plates are commercially available, for example, from Strategene Corp. (La Jolla, Calif.) and Corning Inc. (Acton, Mass.) and include, for example, 48-well, 96-well, 384-well and 1536-well plates.

If desired, cell viability can be determined prior to the assay, for example, using standard techniques including histology, quantitative assessment with radioisotopes, visual observation using a light or scanning electron microscope or a fluorescent microscope. Alternatively, cell viability may be assessed by Fluorescence-Activated Cell Sorting (FACS).

In embodiments where the kinase of interest is a non-constitutively active kinases, phosphorylation of a substrate molecule occurs in response to an extracellular or other type of stimulus, herein termed "kinase activator". Accordingly, in certain embodiments, the inventive assays include exposing the cells to a kinase activator under conditions and for such a time that activation of the kinase can take place and result in phosphorylation of the substrate (in the absence of inhibitors). A kinase activator for use in the practice of the methods of the invention may be any of a variety of stimuli including environmental stress signals, chemical stress signals, biochemical stimuli, and any combinations of such stimuli. As can be appreciated by one of ordinary skill in the art, selection of a kinase activator for the development of an assay according to the present invention will be governed by the nature of the kinase whose activity is to be assessed in the presence of the candidate compound.

In embodiments that relate to a kinase that is constitutively active, i.e., a kinase that exhibits the ability to catalyze the phosphorylation of a substrate molecule in the absence of stimulation, the methods of the invention will not involve kinase stimulation using a kinase activator.

In certain methods of the invention, exposing cells to a reagent, contacting cells with a reagent, or incubating cells with a reagent comprises adding the reagent to a container (e.g., a well of a multi-well plate) containing cells and incubating the cells in the presence of the reagent in a suitable culture medium under conditions and for a period of time such that the intended role of the particular reagent is or can be achieved. More specifically, exposing cells to a kinase activator is preferably carried out under conditions that allow the (non-constitutively active) protein kinase of interest to be activated and the substrate molecule to be phosphorylated in the absence of inhibitors. Exposing cells to a candidate compound to be tested for its effects on the activity of a given kinase is preferably carried out under conditions that allow a known inhibitor of such kinase activity to exert its effects. Such conditions are either well known in the art or may be readily determined, for example, empirically, by one of ordinary skill in the art.

In certain embodiments, the assay and screening methods of the invention may comprise a step of starving the cells before exposing them to different reagents. Cell starvation may be particularly useful when the protein kinase of interest is not constitutively active. Starving of the cells may be performed by any suitable method, for example by culturing the cells in a medium without serum or growth supplements. In certain embodiments, the assay and screening methods of the invention may include fixing the cells. This step is generally performed to preserve or "freeze" a cell in a certain state, preferably so that an accurate representation of the structure of the cell is maintained. For example, it is often desirable to maintain the cell's original size and shape, to minimize loss of cellular materials, and/or to retain the reactivity and/or status of its intracellular constituents. Cells may be fixed by any of a variety of suitable chemical and physical methods well known in the art. In certain embodiments, the assay and screening methods of the invention include a step of permeabilization of the cells. Permeabilization is performed to facilitate access to cellular cytoplasm or intracellular molecules, components or structures of a cell. In particular, permeabilization may allow an agent to enter a cell and reach a concentration within the cell that is greater than that which would normally penetrate into the cell in the absence of such permeabilizing treatment. Permeabilization of the cells may be performed by any suitable method including but not limited to, exposure to a detergent or to an organic alcohol.

B. Candidate Compounds

The screening methods of the invention may be used for identifying compounds or agents that have the ability to inhibit the activity of at least on kinase identified in the invention. Screening according to the present invention is generally performed with the goal of developing therapeutics useful in the prevention and/or treatment of HCV infection and/or HCV-related diseases.

As will be appreciated by those of ordinary skill in the art, any kind of compounds or agents can be tested using the inventive methods. A candidate compound may be a synthetic or natural compound; it may be a single molecule or a mixture or complex of different molecules. In certain embodiments, the inventive methods are used for testing one or more compounds. In other embodiments, the inventive methods are used for screening collections or libraries of compounds. As used herein, the term "collection" refers to any set of compounds, molecules or agents, while the term "library" refers to any set of compounds, molecules or agents that are structural analogs.

Traditional approaches to the identification and characterization of new and useful drug candidates generally include the generation of large collections and/or libraries of compounds followed by testing against known or unknown targets. Both natural products and chemical compounds may be tested by the methods of the invention.

Natural product collections are generally derived from microorganisms, animals, plants, or marine organisms; they include polyketides, non-ribosomal peptides, and/or variants (non-naturally occurring) thereof. Chemical libraries often consist of structural analogs of known compounds or compounds that are identified as "hits" or "leads" via natural product screening. Chemical libraries are relatively easy to prepare by traditional automated synthesis, PCR, cloning or proprietary synthetic methods.

Collection of natural compounds in the form of bacterial, fungal, plant and animal extracts are available from, for example, Pan Laboratories (Bothell, Wash.) or MycoSearch (Durham, N.C.). Libraries of candidate compounds that can be used in the practice of the present invention may be either prepared or purchased from a number of companies. Synthetic compound libraries are commercially available from, for example, Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means.

Useful inhibitors of the activity of kinases of the invention may be found within numerous classes of chemicals, including small molecules, antibodies, peptides, nucleic acid molecules, saccharides, steroids, and the like. In certain embodiments, the methods of the invention are used for identifying compounds or agents that are small molecules. In other embodiments, the invention methods are used for screening small molecule libraries. Preferred small organic molecules have a molecule weight of more than about 50 and less than about 2,500 Daltons; preferably less than 600-700 Daltons; more than preferably less than about 350 Daltons.

Candidate compounds to be tested and screened by the assays of the invention can be compounds previously unknown to have any pharmacological activity, or can be pharmacological agents already known in the art. In particular, as mentioned above, candidate compounds can be selected among agents or derivatives of agents already known in the art to inhibit kinase activity. For example, the purine ring system is considered as a good starting point in the search for inhibitors of various protein kinases and a 2,6,9-trisubstituted purine library has been developed for such purpose (see, for example, P. Shultz, Science, 1998, 281: 533-538; and Y. T. Chang et al., Chem. Biol. 1999, 6: 361-375). Similarly, the conserved and extremely well characterized nature of the ATP binding pocket is one of the most common and successful target for kinase inhibition. Thus, libraries of compounds targeting ATP have been generated and can be used in the screening methods of the invention. Alternatively, candidate compounds can be selected among drugs or derivatives of drugs known in the art to be useful in the treatment of diseases or pathophysiological conditions associated or suspected to be associated with abnormal cellular responses triggered by kinase-mediated events.

The screening of libraries according to the inventive methods will provide "hits" or "leads", i.e., compounds that possess a desired but not-optimized biological activity. The next step in the development of useful drug candidates usually comprises the analysis of the relationship between the chemical structure of a hit compound and its biological or pharmacological activity. Molecular structure and biological activity are correlated by observing the results of systemic structural modification on defined biological endpoints. Structure-activity relationship information available from the first round of screening can then be used to generate small secondary libraries which are subsequently screened for compounds with higher affinity. The process of performing synthetic modifications of a biologically active compound to fulfill stereoelectronic, physicochemical, pharmacokinetic, and toxicologic factors required for clinical usefulness is called lead optimization. The candidate compounds identified by the screening methods of the invention can similarly be subjected to a structure-relationship analysis, and chemically modified to provide improved drug candidates. The present invention also encompasses these improved drug candidates.

C. Identification of Inhibitors of Kinase Activity

According to the screening methods of the present invention, determination of the ability of a candidate compound to inhibit the activity of a kinase of interest includes measurement of the activity of the kinase or of at least one factor that is representative of the kinase activity. Methods for the determination of the activity of a kinase are known in ht the art. Factors representative of the activity of a kinase may be any suitable factor including, but not limited to, amount of kinase expressed, amount of phosphorylated kinase substrate, modifications of cell properties due to phosphorylation of the kinase substrate, and the like.

In an inventive screening method, a candidate compound is identified as an inhibitor of a kinase of interest if the kinase activity is lower in the presence of the candidate compound than in the absence of the candidate compound, or if the factor representative of the kinase activity is different (higher or lower depending on the relationship between the factor and kinase activity) in the presence and in the absence of the candidate compound.

Reproducibility of the results may be tested by incubating cells (for example in more than one well of an assay plate) with the same concentration of the same candidate compound. Additionally, since candidate compounds may be effective at different concentrations depending on the nature of the compound and the nature of its mechanism(s) of action, varying concentrations of the candidate compound may be added to different wells containing cells. Generally, concentrations from about 1 fM to about 10 mM are used for screening. Preferred screening concentrations are between about 10 pM and about 100 µM. Furthermore, screening different concentrations of a candidate compound according to the methods of the invention allows the $IC_{50}$ value to be determined for that compound.

In certain embodiments, the methods of the invention further involve the use of one or more negative or positive control compounds. A positive control compound may be any molecule, agent, or drug that is known to inhibit the activity of the kinase under investigation in the screening method. A negative control compound may be any molecule, agent, or drug that is known to have no effect on the activity of the kinase under investigation. In these embodiments, the invention methods further comprise comparing the effects of the candidate compound to the effects (or absence thereof) of the positive or negative control compound. Such negative and positive control compounds are known in the art or may be identified by the methods described herein or by any other kinase assay.

As already mentioned above, a compound identified as an inhibitor of a kinase of interest may inhibit the kinase activity through a single mechanism of action. Alternatively, it may inhibit the kinase activity through a combination of different mechanisms of action. For example, the compound may inhibit (e.g., by precluding, reversing or disrupting) the binding of the kinase activator to its cell-surface receptor. Alternatively, the compound may favor or stimulate the binding of the kinase activator to its cell-surface receptor. The compound may, additionally or alternatively, prevent or favor activation of a downstream intracellular protein kinase and/or its may affect the transfer of a phosphate group to a substrate molecule.

D. Characterization of Candidate Inhibitors of Kinase Activity

As will be appreciated by those skilled in the art, it is generally desirable to further characterize kinase inhibitors identified by the inventive screening methods or kinase inhibitors already known in the art.

For example, if a candidate compound has been identified as an inhibitor of the activity of a kinase of interest in a cell culture system (e.g., an established cell line), it may be desirable to test this ability in a different cell culture system (e.g., primary or secondary cells). Alternatively or additionally, it may be desirable to directly test the effect of the compound on the HCV entry into cells and/or HCV infection of cells (see, for instance, Example 2 which describes the use of a HCVpp system and a HCVcc system). It may also be desirable to perform pharmacokinetics and toxicology studies.

Candidate compounds identified as kinase inhibitors by screening methods of the invention may also be further tested in assays that allow for the determination of the compounds' properties in vivo. Suitable animal models include, but are not limited to, chimeric transgenic mice repopulated with human hepatocytes that have been developed for the study of HCV infection (Mercer, 2001). These animals are derived by transplantation of normal human hepatocytes into SCID mice carrying a plasminogen activator transgene (Alb-uPA). The expression of the Alb-uPA transgene is cytotoxic to mouse hepatocytes favoring hepatocyte engraftment. Backcrossing with the SCID mice allow the engraftment and repopulation by xenogeneic hepatocytes. Once human hepatocytes are stably engrafted in the SCID/Alb-uPA mouse, these animals can be infected with human hepatotrophic viruses including hepatitis C. The human SCID/Alb-uPA mouse model has been successfully used to study the efficacy of neutralizing antibodies for control of HCV infection (Law, 2008) as well as antivirals (Vanwolleghem, 2007). Other mouse models include transgenic mice expressing HCV proteins (for a review see Barth, 2008) and the chimpanzee (Kato, 2008).

The systems described herein may be formulated into kits. For example, cells expressing one or more of the kinases disclosed herein or cells expressing one or more of the kinases disclosed herein and capable of sustaining HCV replication, or cell lysates thereof, can be packaged in a variety of containers, e.g., vials, tubes, microtitre well plates, bottles, and the like. Other reagents can be included in separate containers and provided with the kit, e.g., positive control samples or compounds, negative control samples or compounds, buffers, cell culture media, specific detection probes, and the like.

IV—Treatment or Prevention of HCV Infection and HCV-Associated Diseases

The present invention relates to novel therapeutic protocols for the treatment and/or prevention of HCV infection and/or HCV-related diseases, which are designed to target at least one of the human protein kinases identified as targets by the Applicants. More specifically, the present invention provides methods for treating or preventing HCV infection or a HCV-related disease in a subject, comprising a step of administering to the subject an effective amount of an agent that inhibits the activity of a kinase identified in the present invention.

A. Indications

Protein kinase inhibitors of the present invention may be used in therapeutic and prophylactic methods to treat and/or prevent HCV infection, or to treat and/or prevent a liver disease or a pathological condition affecting HCV-susceptible cells, such as liver cells, lymphoid cells, or monocytes/macrophages. In the practice of the present invention, a protein kinase inhibitor interferes with HCV-host cells interactions by inhibiting or suppressing the activity of a kinase of the invention, thereby reducing, inhibiting, blocking or preventing HCV entry into the cell and/or HCV infection of the cell.

Methods of treatment of the present invention may be accomplished using an inventive protein kinase inhibitor or a pharmaceutical composition comprising an inventive protein kinase inhibitor (see below). These methods generally comprise administration of an effective amount of at least one protein kinase inhibitor, or a pharmaceutical composition thereof, to a subject in need thereof. Administration may be performed using any of the methods known to one skilled in the art. In particular, a protein kinase inhibitor or composition thereof may be administered by various routes including, but not limited to, aerosol, parenteral, oral or topical route.

In general, an inventive protein kinase inhibitor or composition will be administered in an effective amount, i.e., an amount that is sufficient to fulfill its intended purpose. The exact amount of kinase inhibitor or pharmaceutical composition to be administered will vary from subject to subject, depending on the age, sex, weight and general health condition of the subject to be treated, the desired biological or medical response (e.g., prevention of HCV infection or treatment of HCV-associated liver disease), and the like. In many embodiments, an effective amount is one that inhibits the activity of the kinase so as to inhibit or prevent HCV from entering into a subject's susceptible cells and/or infecting a subject's cells, thereby preventing HCV infection, treat or prevent liver disease or another HCV-related pathology in the subject.

Protein kinase inhibitors and compositions of the present invention may be used in a variety of therapeutic and prophylactic methods. In particular, the present invention provides a method for treating or preventing a HCV-related liver disease or pathology in a subject, which comprises administering to the subject an effective amount of an inventive protein kinase inhibitor (or composition thereof) which inhibits the activity of a kinase of the invention so as to inhibit HCV from entering or infecting the subject's cells, thereby treating or preventing the liver disease or pathology in the subject. The liver disease or pathology may be inflammation of the liver, liver fibrosis, cirrhosis, and/or hepatocellular carcinoma (i.e., liver cancer associated with HCV infection).

The present invention also provides a method for treating or preventing a HCV-associated disease or condition (including a liver disease) in a subject, which comprises administering to the subject an effective amount of an inventive protein kinase inhibitor (or composition thereof) which inhibits the activity of a kinase of the invention so as to inhibit HCV from entering or infecting the subject's cells, thereby treating or preventing the HCV-associated disease or condition in the subject. In certain embodiments of the present invention, the protein kinase inhibitor or composition is administered to a subject diagnosed with acute hepatitis C. In other embodiments of the invention, the protein kinase inhibitor is administered to a subject diagnosed with chronic hepatitis C.

Administration of an inventive protein kinase inhibitor or composition according to such methods may result in amelioration of at least one of the symptoms experienced by the individual including, but not limited to, symptoms of acute hepatitis C such as decreased appetite, fatigue, abdominal pain, jaundice, itching, and flu-like symptoms; symptoms of chronic hepatitis C such as fatigue, marked weight loss, flu-like symptoms, muscle pain, joint pain, intermittent low-grade fevers, itching, sleep disturbances, abdominal pain, appetite changes, nausea, diarrhea, dyspepsia, cognitive changes, depression, headaches, and mood swings; symptoms of cirrhosis such as ascites, bruising and bleeding tendency, bone pain, varices (especially in the stomach and esophagus), steatorrhea, jaundice and hepatic encephalopathy; and symptoms of extrahepatic manifestations associated with HCV such as thyroiditis, porphyria cutanea tarda, cryoglobulinemia, glomerulonephritis, sicca syndrome, thrombocytopenia, lichen planus, diabetes mellitus and B-cell lymphoproliferative disorders.

Alternatively or additionally, administration of an inventive protein kinase inhibitor or composition according to a method of the invention may slow, reduce, stop or alleviate the progression of HCV infection or an HCV-associated disease, or reverse the progression to the point of eliminating the infection or disease. Administration of an inventive protein kinase inhibitor or composition according to such methods may also result in a reduction of the number of viral infections, reduction of the number of infectious viral particles, and/or reduction in the number of virally infected cells.

The effects of a treatment according to the invention may be monitored using any of the assays known in the art for the diagnosis of HCV infection and/or liver disease. Such assays include, but are not limited to, serological blood tests, liver function tests to measure one or more of albumin, alanine transaminase (ALT), alkaline phosphatase (ALP), aspartate transaminase (AST), and gamma glutamyl transpeptidase (GGT), and molecular nucleic acid tests using different techniques such as polymerase chain reaction (PCR), transcription mediated amplification (TMA), or branched DNA (bDNA).

Protein kinase inhibitors and compositions of the present invention may also be used in immunization therapies. Accordingly, the present invention provides a method of reducing the likelihood of susceptible cells of becoming infected with HCV as a result of contact with HCV. The method comprises contacting the susceptible cells with an effective amount of an inventive kinase inhibitor or composition which inhibits the activity of an inventive kinase so as to inhibit HCV from entering or infecting the susceptible cells, thereby reducing the likelihood of the cells to become infected with HCV as a result of contact with HCV. The present invention also provides a method of reducing the likelihood of a subject's susceptible cells of becoming infected with HCV as a result of contact with HCV. In this method, contacting the susceptible cells with an inventive protein kinase inhibitor or composition thereof may be performed by administering the kinase inhibitor or composition to the subject.

Reducing the likelihood of susceptible cells or of a subject of becoming infected with HCV means decreasing the probability of susceptible cells or a subject to become infected with HCV as a result of contact with HCV. The decrease may be of any significant amount, e.g., at least a 2-fold decrease, more than a 2-fold decrease, at least a 10-fold decrease, more than a 10-fold decrease, at least a 50-fold decrease, more than a 50-fold decrease at least a 100-fold decrease, or more than a 100-fold decrease.

In certain embodiments, the subject is infected with HCV prior to administration of the inventive protein kinase inhibitor or composition. In other embodiments, the subject is not infected with HCV prior to administration of the inventive kinase inhibitor or composition. In yet other embodiments, the subject is not infected with, but has been exposed to, HCV. In certain embodiments, the subject is infected with HIV or HBV.

For example, the methods of the present invention may be used to reduce the likelihood of a subject's susceptible cells of becoming infected with HCV as a result of liver transplant. As already mentioned above, when a diseased liver is removed from a HCV-infected patient, serum viral levels plummet. However, after receiving a healthy liver transplant, virus levels rebound and can surpass pre-transplant levels within a few days (Powers, 2006). Liver transplant patients may benefit from administration of an inventive protein kinase inhibitor that reduces, inhibits, blocks or prevents HCV entry into the cells. Administration may be performed prior to liver transplant, during liver transplant, and/or following liver transplant.

Other subjects that may benefit from administration of an inventive kinase inhibitor or composition include, but are not limited to, babies born to HCV-infected mothers, in particular if the mother is also HIV-positive; health-care workers who have been in contact with HCV-contaminated blood or blood contaminated medical instruments; drug users who have been exposed to HCV by sharing equipments for injecting or otherwise administering drugs; and people who have been exposed to HCV through tattooing, ear/body piercing and acupuncture with poor infection control procedures.

Other subjects that may benefit from administration of an inventive protein kinase inhibitor or composition include, but are not limited to, subjects that exhibit one or more factors that are known to increase the rate of HCV disease progression. Such factors include, in particular, age, gender (males generally exhibit more rapid disease progression than females), alcohol consumption, HIV co-infection (associated with a markedly increased rate of disease progression), and fatty liver.

In certain embodiments, an inventive protein kinase inhibitor or composition is administered alone according to a method of treatment of the present invention. In other embodiments, an inventive kinase inhibitor or composition is administered in combination with at least one additional therapeutic agent. The inventive kinase inhibitor or composition may be administered prior to administration of the therapeutic agent, concurrently with the therapeutic agent, and/or following administration of the therapeutic agent.

Therapeutic agents that may be administered in combination with an inventive kinase inhibitor or composition may be selected among a large variety of biologically active compounds that are known in the art to have a beneficial effect in the treatment, management or prevention of HCV infection, or a HCV-associated disease or condition. Such agents include, in particular, antiviral agents including, but not limited to, interferons (e.g., interferon-alpha, pegylated interferon-alpha), ribavirin, anti-HCV (monoclonal or polyclonal) antibodies, RNA polymerase inhibitors, protease inhibitors, IRES inhibitors, helicase inhibitors, antisense compounds, ribozymes, and any combination thereof.

B. Administration

An inventive protein kinase inhibitor, (optionally after formulation with one or more appropriate pharmaceutically acceptable carriers or excipients), in a desired dosage can be administered to a subject in need thereof by any suitable route. Various delivery systems are known and can be used to administer kinase inhibitors of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocural, and oral routes. An inventive kinase inhibitor or composition may be administered by any convenient or other appropriate route, for example, by infusion or bolus injection, by absorption through epithelial or mucocutaneous linings (e.g., oral, mucosa, rectal and intestinal mucosa, etc). Administration can be systemic or local. Parenteral administration may be preferentially directed to the patient's liver, such as by catheterization to hepatic arteries or into a bile duct. As will be appreciated by those of ordinary skill in the art, in embodiments where an inventive protein kinase inhibitor is administered in combination with an additional therapeutic agent, the kinase inhibitor and therapeutic agent may be administered by the same route (e.g., intravenously) or by different routes (e.g., intravenously and orally).

C. Dosage

Administration of an inventive kinase inhibitor (or composition) of the present invention will be in a dosage such that the amount delivered is effected for the intended purpose. The route of administration, formulation and dosage administered will depend upon the therapeutic effect desired, the severity of the HCV infection or HCV-related condition to be treated if already present, the presence of any other infection, the age, sex, weight and general health condition of the patient as well as upon the potency, bioavailability, and in vivo half-life of the kinase inhibitor or composition used, the use (or not) of concomitant therapies, and other clinical factors. These factors are readily determinable by the attending physician in the course of the therapy. Alternatively or additionally, the dosage to be administered can be determined from studies using animal models (e.g., chimpanzee or mice). Adjusting the dose to achieve maximal efficacy based on these or other methods are well known in the art and are within the capabilities of trained physicians. As studies are conducted using the inventive kinase inhibitors, further information will emerge regarding the appropriate dosage levels and duration of treatment.

A treatment according to the present invention may consist of a single dose or multiple doses. Thus, administration of an inventive kinase inhibitor, or composition thereof, may be constant for a certain period of time or periodic and at specific intervals, e.g., hourly, daily, weekly (or at some other multiple day interval), monthly, yearly (e.g., in at time release form). Alternatively, the delivery may occur at multiple times during a given time period, e.g., two or more times per week; two or more times per month, and the like. The delivery may be continuous delivery for a period of time, e.g., intravenous delivery.

In general, the amount of kinase inhibitor administered will preferably be in the range of about 1 ng/kg to about 100 mg/kg body weight of the subject, for example, between about 100 ng/kg and about 50 mg/kg body weight of the subject; or between about 1 µg/kg and about 10 mg/kg body weight of the subject, or between about 100 µg/kg and about 1 mg/kg body weight of the subject.

V—Pharmaceutical Compositions

As mentioned above, protein kinase inhibitors of the invention may be administered per se or as a pharmaceutical composition. Accordingly, pharmaceutical compositions are provided that comprise an effective amount of a kinase inhibitor described herein and at least one pharmaceutically acceptable carrier or excipient. In some embodiments, the composition further comprises one or more additional biologically active agents.

Inventive kinase inhibitors and pharmaceutical compositions may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of an inventive kinase inhibitor for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient (here a kinase inhibitor), it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly (orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the kinase inhibitor, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizers or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive kinase inhibitor may be mixed with at least one inert, physiologically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment (e.g., the liver). This may be achieved, for example, and not by way of limitation, by local infusion during surgery (e.g., liver transplant), topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., a kinase inhibitor) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

When a pharmaceutical composition of the present invention is used as "vaccine" to prevent HCV-susceptible cells to become infected with HCV, the pharmaceutical composition may further comprise vaccine carriers known in the art such as, for example, thyroglobulin, albumin, tetanus toxoid, and polyamino acids such as polymers of D-lysine and D-glutamate. The vaccine may also include any of a variety of well known adjuvants such as, for example, incomplete Freund's adjuvant, alum, aluminium phosphate, aluminium hydroxide, monophosphoryl lipid A (MPL, GlaxoSmithKline), a saponin, CpG oligonucleotides, montanide, vitamin A and various water-in-oil emulsions prepared from biodegradable oils such as squalene and/or tocopherol, Quil A, Ribi Detox, CRL-1005, L-121 and combinations thereof.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18$^{th}$ Ed., 1990, Mack Publishing Co.: Easton, Pa.

B. Additional Biologically Active Agents

In certain embodiments, a kinase inhibitor is the only active ingredient in a pharmaceutical composition of the present invention. In other embodiments, the pharmaceutical composition further comprises one or more biologically active agents. Examples of suitable biologically active agents include, but are not limited to, vaccine adjuvants and therapeutic agents such as anti-viral agents (as described above), anti-inflammatory agents, immunomodulatory agents, analgesics, antimicrobial agents, antibacterial agents, antibiotics, antioxidants, antiseptic agents, and combinations thereof.

Anti-viral agents suitable for use in the practice of the present invention include, but are not limited to, those which have an effect on the same protein kinase, those which have an effect on a different target molecule (i.e., not a protein kinase or not the same protein kinase), including those target molecules that are involved in viral entry, in viral internalization, in viral replication and/or in viral release, those which prevent or reduce the occurrence of viral resistance, and the like. The kinase inhibitors of the present invention may also be used in combination with agents which induce IFN expression.

The antiviral combinations of the present invention provide a means of treatment which may not only reduce the effective dose of either drug required for antiviral activity, thereby reducing toxicity, but may also improve the absolute antiviral effect as a result of attacking the virus through multiple mechanisms. Similarly, the combinations provide a means for circumventing the development of viral resistance to a single therapy, thereby providing a more efficient treatment.

In the pharmaceutical compositions of the present invention, the kinase inhibitor and additional therapeutic agent(s) may be combined in one or more preparations for simultaneous, separate or sequential administration of the kinase inhibitor and therapeutic agent(s). More specifically an inventive composition may be formulated in such a way that the kinase inhibitor and therapeutic agent(s) can be administered together or independently from each other. For example, a kinase inhibitor and a therapeutic agent can be formulated together in a single composition. Alternatively, they may be maintained (e.g., in different compositions and/or containers) and administered separately.

C. Pharmaceutical Packs or Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of a kinase inhibitor of the present invention.

Different ingredients of a pharmaceutical pack or kit may be supplied in a solid (e.g., lyophilized) or liquid form. Each ingredient will generally be suitable as aliquoted in its respective container or provided in a concentrated form. Pharmaceutical packs may include media for the reconstitution of lyophilized ingredients. Individual containers of the kits will preferably be maintained in close confinement for commercial sale.

In certain embodiments, a pharmaceutical pack or kit includes one or more additional therapeutic agent(s) (e.g., one or more anti-viral agents, as described above). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data are actually obtained.

Some of the results reported below were presented at the 15th International Symposium on Hepatitis C Virus and Related Viruses (San Antonio, Tex., USA, 5-9 Oct. 2008) and are summarized in an Abstract entitled "Identification of cellular kinases as co-factors for hepatitis C virus entry using a functional high-throughput siRNA screen" by J. Lupberger et al. Other results reported below are the subject of a manuscript (J. Lupberger et al., "Genome-wide analysis of human kinases as host factors for hepatitis C virus entry") that was submitted to Molecular Systems Biology.

Example 1

Preliminary Identification of Host Cell Kinases as Co-Factors for HCV Entry

1. Materials and Methods

Cells and Replicons.

HEK 293T, Huh7 and Huh7.5.1 cells used in the present study have previously been described (Bartosch, 2003; Barth, 2003; Zhong, 2005). Primary human hepatocytes were isolated and cultured as previously described (David, 1998, which is incorporated herein by reference in its entirety). Subgenomic HCV replicon JFH1-SGR used herein has also previously been described (Kato, 2005).

Production of Retroviral HCV and VSV Pseudoparticles.

HCVpp derived from H77 and VSVpp derived were generated as previously described (Bartosch, 2003; Barth, 2006). Pseudoparticles (pp) without envelope glycoproteins (control pp) were used as negative control (Barth, 2003). The HCVpp and VSVpp preparations were adjusted in order to obtain equal luciferase activities after Huh7 infection.

Production of Recombinant HCV and Infection Assays.

Bicistronic plasmid pFK-Luc-Jc1 (Koutsoudakis, 2006) encodes a luciferase reporter gene and a chimeric HCV genome designated Jc1 which consists of J6CF and JFH1 segments. In vitro HCV RNA synthesis and RNA transfection were carried out as previously described (Wakita, 2005). Culture supernatants from transfected cells were cleared and concentrated as previously described using an Amicon Ultra 15 (Millipore, USA) and used directly or were stored at 4° C. or −80° C. Viruses were titrered by using the limiting dilution assay on Huh7.5.1 cells with a few minor modifications and TCID50 values were calculated based on a method previously described (Lindenbach, 2005).

High-Throughput Gene Silencing Using siRNA.

The Human Kinase siRNA Set Version 2.0 (Qiagen, Germany) consists of 691 pools of 4 independent siRNA/target genes and was applied to silence 691 cellular kinases and associated proteins in Huh7 cells. 5,000 cells/0.3 cm$^2$ were reverse-transfected with 3.5 μmol siRNA using 1 μL Interferrin transfection agent (Polyplus, France). 72 hours post-transfection, supernatants were removed and the cells were infected side-by-side with 50 μL HCVpp and VCVpp. 100 μL of fresh cell culture medium was added after 6 hours of incubation at 37° C., and 48 hours post-infection, the complete cell culture supernatant was removed and cells were lysed using 100 μL of Glo lysis buffer (Promega, USA). Firefly luciferase activity was measured 10 minutes after cell lysis using 25% (v/v) Bright-Glo luciferease substrate (Promega, USA) by a high-throughput luminometer (Berthold, Germany). Specific infectivity was assessed by total protein normalization using the Dc protein assay kit (Biorad, USA).

Identification of Novel HCV Entry Factors.

The impact of gene silencing was defined by an increase or decrease of HCVpp entry compared to cells transfected with nonspecific siRNA. In depth, statistical analysis was performed as previously described (Ploner, 2006; Raffelsberger, 2008; Wettenhall, 2004) to ensure a maximum reduction of false positives (type I error) without penalizing the true positive test results (type II error). HCV specific impact on HCV entry was determined as the absence of a significant similar effect on entry of a control virus (VSVpp) performed in a side-by-side experiment (HCV specific effect: HCV entry significantly decreased and VSVpp entry significantly unchanged or increased—and vice versa). Additionally, protein kinases with a potential general importance to viral entry mechanisms were identified for which the silencing of the corresponding genes resulted in a marked reduction of HCV viral entry (equivalent to >80% inhibition of HCV entry, if the reproductivibility is statistically significant) into cells with no regard to changes caused by gene silencing to VSVpp entry. The impact of the identified candidate kinases on the infectious HCV life cycle was verified by a second siRNA screen measuring the effect of candidate gene silencing on HCVcc infection as described for the pp-siRNA screen above. Moreover, to ensure specificity of the second HCVcc-siRNA screen, an MTT-cytotoxicity test of the transfected siRNA was performed side-by-side as previously described (Cole, 1986).

Inhibition of HCV Infection Using Protein Kinase Inhibitors.

All inhibitors used in this study were obtained from LC Laboratories (USA). Before use, they were dissolved in DMSO and diluted in Huh7.5.1 cell culture medium (Zhong, 2005). Following incubation, HCVpp entry and HCVcc infection were assessed by luciferase reporter gene expression or RT-PCR of HCV RNA in cells as previously reported (Pestka, 2007; Zeisel, 2007).

Northern Blotting.

A 9.7 kb fragment derived from plasmid JKH1 (Wakita, 2005) digested with XbaI and EcoRI was labeled with $\alpha^{32}$P-CTP using NEBlot kit (NEB, USA). Northern blotting was performed according to standard protocols (F. M. Ausubel et al., "Current Protocols in Molecular Biology", John Wiley 1 Sons, Inc., 2007).

2. Identification of Host Cell Kinases as Co-Factors for HCV Entry

Using a state-of-the-art, functional high-throughput siRNA HCVpp entry screen, the present Applicants have identified two panels of host cell kinases. The kinases of the first panel exhibit a significant and specific inhibition of HCVpp entry without affecting the entry of non-relating control virus (VSVpp). The kinases of the second panel exhibit a marked inhibition of HCVpp entry/infection with no regard to changes caused by gene silencing to VSVpp entry.

By applying the selection criteria, silencing of 69 out of the 691 genes of kinases and associated proteins resulted in a specific functional impact on HCVpp entry without affecting entry of an unrelated control virus (VSVpp). These 69 kinases, which are presented in FIG. 1, are: FGR, CHUK, PSKH1, DGKB, ILK, CKS1B, PLK3, GKAP1, CALM2, RPS6KA5, MAGI1, LTK, ITPKA, PIP5K2A, ADK, STK11, CDKN1B, CHKB, BUB1B, STK38, TYK2, PRKCABP, EGFR, CSK, AK3, FER, PRKD2, CDKL3, PDIK1L, CKMT1, CDKN2C, CDK2, CAMK2G, EPHB4, GAK, PACSIN2, SGK2, DCAMKL1, MAP3K13, IRAK2, ARAF, PAK4, MAPK7, ATR, SRC, PTK2B, EPHB1, BCR, EPHA2, PIP5K2B, CDK3, STK24, MKNK2, PKMYT1, FES, ACVR2B, MAP2K1IP1, APEG1, JAK1, AURKB, CHKA, PRKACG, DDR2, PIK3C2A, ADRBK1, CALM3, FASTK, WEE1 and JAK2. The number of identified kinases matching the selection criteria corresponds to 10% of the total number of genes investigated. Interestingly, the identified molecules comprise 9 kinases accessible to therapeutic intervention by established drugs. These 9 kinases are: CHUK, EGFR, CDK2, EPHB4, SRC, BCR, EPHA2, CDK3, and AURKB.

Silencing of 32 out of the 691 kinases resulted in extreme inhibition of HCV entry with no regard to changes caused by gene silencing to VSVpp entry. These 32 kinases, which are presented in FIG. 2, are: FN3K, CIB2, BCKDK, NEK9, STK33, BRAF, STK22C, PI4KII, RIOK1, CKB, Sharpin, RPS6KL1, FLT3LG, HIPK3, CDC2, ERBB4, CDC2L1, PANK3, SKIP, MAP4K5, ATM, CDK4, KIAA1446, BMP2K, BMX, CDK8, TNK2, NEK4, EPHA3, FGFR4, MAP3K7IP1 and MAPKAP1. The number of identified kinases matching the selection criteria corresponds to about 5% of the total number of genes investigated. The identified molecules comprise 5 kinases accessible to therapeutic intervention by established drugs, i.e.: BRAF, CDC2, ERBB4, CDK4, and CDK8.

To confirm the functional impact of the candidate molecules identified by the screen for HCV entry, the Applicants have analyzed the impact of the identified gene products on infection of hepatoma cells using HCVpp of different genotypes as well as cell culture-derived infectious HCV (HCVcc). As an example of the reliability and viability of the identification of HCV co-entry factors by the siRNA HCVpp entry screen, the Applicants have demonstrated that silencing of kinase EphA2 markedly and specifically inhibited entry of HCVpp derived from all major genotypes and markedly inhibited HCVcc infection of Huh7.5 human hepatoma cells.

Interestingly, the protein kinase EphA2 has been shown to modulate permeability of cellular tight junctions by phosphorylation of a member of the Claudin (CLDN) protein family (Tanaka, 2005) and HCV non-structural protein NS4B upregulates EphA2 expression (Zheng, 2005). EphA2 is expressed in the liver as well as in primary human hepatocyte and human hepatoma cell lines. This is of major interest for the molecular understanding of HCV entry, since members of the claudin family have been shown to represent key host co-factors for HCV infection in Huh7 hepatoma cells (Evans, 2007; Meertens, 2008).

3. Kinase Inhibitors for the Inhibition of HCV Entry and Infection

The identification of EphA2 as putative HCV co-entry factor is also of interest for the development of novel antiviral strategies targeting HCV entry since EphA2 has been shown to be a target of Dasatinib (Huang, 2007), a clinically licensed kinase inhibitor for the treatment of chronic myeloid leukemia.

To study whether Dasatinib—a protein kinase inhibitor targeting EphA2—results in inhibition of HCV entry and infection, the Applicants have incubated hepatoma cells with Dasatinib and subsequently studied its effect on HCVpp entry and HCVcc infection. Dasatinib was found to markedly inhibit HCVpp entry (H77c strain—genotype 1a) and HCVcc infection (JFH-1 strain—genotype 2a) in a dose-dependent manner and at concentrations similar to concentrations achieved during clinical use for the treatment of haematological malignancies.

Further analysis using HCV subgenomic replicons (JFH1 strain, Kato, 2005) demonstrated that Dasatinib was indeed specifically targeting HCV entry and not virus-host interactions during viral replication.

Similar results were obtained using inhibitors targeting epidermal growth factor receptor (EGFR) that was also identified as co-factor for HCV entry by the present study. Erlotinib, Vandetanib, Gefitinib or Lapatinib were found to markedly inhibit HCVcc infection of huh7.5.1 cells in a dose-dependent manner and at concentrations similar to therapeutic concentrations achieved during clinical use (see FIG. 3).

In conclusion, a panel of host cell kinases has been identified as novel HCV co-factors, including EphA2 and members of the EGF receptor family. Furthermore, HCV-kinase interaction represents a novel and original target for therapeutic interventions against HCV infection as shown by efficient inhibition of HCV entry and infection by the protein kinase inhibitor Dasatinib.

Example 2

Refined Identification of Host Cell Kinases as Co-Factors for HCV Entry

1. Materials and Methods
Reagents and Antibodies.

Human Kinase siRNA Set Version 2.0 (pool of four siRNAs) and individual siRNAs were obtained from Qiagen. Erlotinib (Tarceva®), Dasatinib (Sprycel®), Gefitinib (Iressa®), Vandetanib (Zactima®) and Lapatinib (Tykerb®) were obtained from IC Laboratories, TpIII kinase inhibitor and Wortmannin from Calbiochem, Flavopiridol and Dorsomorphin from Sigma-Aldrich. Anti-EphA2 C-20 and protein A/G-agarose beads were obtained from Santa Cruz Biotechnologies, and -EGFR from Millipore and alkaline-phosphatase labelled secondary antibodies from GE Healthcare.
Cell Lines, Primary Hepatocytes and Replicons.

Same as above.
Genome-wide RNAi Kinase HCV Entry Screen.

Screening was performed at the Transfected Cell Array (TCA) platform, Institut de Génétique et de Biologie Moléculaire et Cellulaire (IGBMC) in Illkirch, France. The library used for this screen was the Human Kinase siRNA Set Version 2.0 (pool of four siRNA) from Qiagen. Individual siRNAs were obtained from Qiagen. A functional HCV entry siRNA screen targeting 691 cellular kinases and associated proteins was established as outlined in FIG. 4. For each target 3.5 pmol siRNA was reverse-transfected in 5,000 Huh7 cells/ 0.3 cm$^2$ using Interferrin (Polyplus). The effect of gene silencing on viral entry was investigated three days after siRNA transfection using HCV pseudotyped particles (HCVpp H77C; genotype 1a) (Bartosh, 2003; Pestka, 2007) harboring a luciferase reporter gene. Impact on VSVpp entry was analyzed side-by-side. Virus entry was assessed two days after infection by measuring reporter gene luciferase activity in cell lysates using the Bright Glo Luciferase assay system (Promega) with a Mithras LB 940 luminometer (Berthold Technologies). Hits were validated independently using four different single siRNAs from the same siRNA library (Qiagen) silencing the same target mRNA. Validation using HCVcc strain Luc-Jc1 (Dimitrova, 2008; Pietschmann, 2006) (TCID$_{50}$ approximately 10$^3$/mL) was performed in Huh7.5.1 cells using the same protocol as described above. All siRNA screens were performed in 96 well cell culture plates. Luciferase results were normalized by protein content of the lysates using Dc protein assay (Bio-Rad). To minimize non-specific effects due to evaporation, outside wells were not used for the screens but were filled with phosphate buffered saline (PBS). Non-specific effects of gene silencing due to changes in cell proliferation were normalized by measuring the protein content of the individual well. The quality of the established high-throughput screens, the individual plate designs as well as the amount of replicates were assessed in pilot experiments by calculating the Z-factor (Zhang, 1999). The HCVpp screens (Z=0.37) were performed in duplicates with 60 of 96 central plate positions used for the screen. The HCVcc validation screens (Z=0.47) were performed in triplicates with 32 of 96 central plate positions used for the screen. As an internal quality control of gene silencing and HCVpp and HCVcc infection, positive and negative control siRNAs (GFP, CD81) were transfected side-by-side on each plate. Cytotoxic effects on cells were assessed in triplicates by analyzing the ability to metabolize 3-(4,5-dimethylthiazol-2-yl)-2,5-diphenyltetrazolium bromide (MTT) as described below.
High-Throughput Screening:

Hit Selection. The impact of gene silencing was defined by an increase or decrease of HCVpp entry expressed as the ratio of entry compared to the experimental mean value of entry into control transfected (siRNA targeting GFP). HCV specificity was determined as the absence of a significant similar impact on entry of VSVpp control virus. The log 2-ratios were tested for difference to 0 using the empirical Bayes procedure implemented in Bioconductor (Gentleman, 2004) package limma (Wettenhall, 2004) in order to ensure a maximum reduction of false positives (type I error) without penalizing the true positive test results (type II error) (Allison, 2006). Resulting B-values from empirical Bayes testing were examined for their distribution in order to define meaningful cut-offs (not shown). Finally, for HCVpp a threshold of −3.5 (corresponding to a maximum p-value of 4×10$^{-4}$), for HCVpp a threshold of −4.4 (corresponding to a maximum of p-value of 3×10$^{-6}$) and for VSVpp a threshold of −3.6 (corresponding to a maximum of p-value of 1.1×10$^{-3}$) were chosen as stringent parameters based on the underlying frequency distributions (data not shown). Genes (29 in total) exhibiting an intense effect on HCVpp entry (B-value>5) with no regard on entry of VSVpp were also included for further validation. In addition, the local false discovery rates (fdr) for all comparisons for each gene were determined using the library "fdrtool" (Strimmer, 2008). For validation, 10 additional genes also were included that decreased HCV entry by ≥2 SDs from the plate mean (i.e., the strategy used by Brass, 2008) but that would not have been identified by the approach followed by the present Applicants due to the fact that high intra variability gives only high p-values or low corresponding B-values. To exclude off-target effects by pooled siRNAs, candidates were validated if HCV entry was reduced by ≥50% compared to control transfected cells by at least two individual siRNAs.
Gene Ontology and Gene Annotation.

Gene ontology terms and gene associations were obtained from Human Kinase siRNA Set Version 2.0 validated by Ingenuity Pathways database (Mountainview, Calif., USA). Biological function analysis of the identified kinases was performed using Ingenuity Pathways database (Krishnan, 2008; Tuvin, 2009). Biological function terms were accepted if they were significantly enriched with a p-value<10$^{-5}$. Additionally, the identified hits were analyzed for known and predicted protein interactions using STRING mega-database that maps all interaction evidence onto a common set of genomes and proteins (Jensen, 2009).
Analysis of Kinase Expression by Immunoprecipitation and Immunoblot.

Immunoprecipitation of EphA2 was performed following lysis of transfected cells using a buffer containing 50 mM Tris, pH 8, 150 mM NaCl, 1% NP-40, and protease inhibitor cocktail (Roche). For immunoprecipitation, 2.5 μg of anti-EphA2 C-20 antibody (180 μg protein content) and 25 μL of protein A/G beads (Santa Cruz Biotechnologies) were used. Western blot was performed following GE Healthcare protocols using Hybond-P membranes and visualized using ECF substrate and Typhoon Trio high performance fluorescence scanner (GE Healthcare).

Infection of Huh7-Derived Cell Lines and Primary Human Hepatocytes with HCVpp and HCVcc.

HCVpp (strains H77C, HCV-J, UKN2A.2.4, UKN3A, UKN4A.21.16, VD, VH, VK, VN), VSPpp and HCVcc (strains Jc1, Luc-Jc1) were produced as previously described (Bartosch, 2003; Dimitrova, 2008; Fati-Kremer, 2009; Pestka, 2007; Pietschmann, 2006; Tan, 2006; and Zeisel, 2007). Infection of Huh7, Huh7.5 cells and human hepatocytes with HCVpp derived from strains H77C (1a), and HCVcc derived from strains Jc1 (2a/2a) and Luc-Jc1 (2a/2a) ($TCID_{50}$ $10^3$/mL) was performed as described (Dimitrova, 2008; Fati-Kremer, 2009; Lan, 2008; Meunier, 2008; and Zeisel, 2007). Gene silencing was performed 3 days prior infection as described for the RNAi screen. Protein kinase inhibitors (with the exception of Wortmannin, 1% DMSO final) were applied at a final solvent concentration of 0.25% DMSO Inhibitors were added to the cell culture medium 1 jour prior HCVpp or HCVcc infection.

Analysis of HCV Replication.

Electroporation of RNA derived from plasmids pSGR-JFH1 was performed as previously described (Lan, 2008). Four hours after electroporation, cells were incubated with protein kinase inhibitors in cell culture supernatant for 24 hours. Total RNA was isolate and analyzed by Northern blot analysis of HCV RNA as described (Lohmann, 1999).

Toxicity Assays. Cytotoxicity effects on cells were assessed in triplicates by analyzing the ability to metabolize 3-(4,5-dimethylthiazol-2-yl)-2,5-diphenyltetrazolium bromide (MTT) (Lan, 2008). For siRNA experiments, MTT was added 3 days after transfection with siRNA for 5 hours. The final concentration of MTT was 0.6 mg/mL. Formazan crystals produced by the cells were solubilized and measured as described (Mosmann, 1983).

Figure 4:
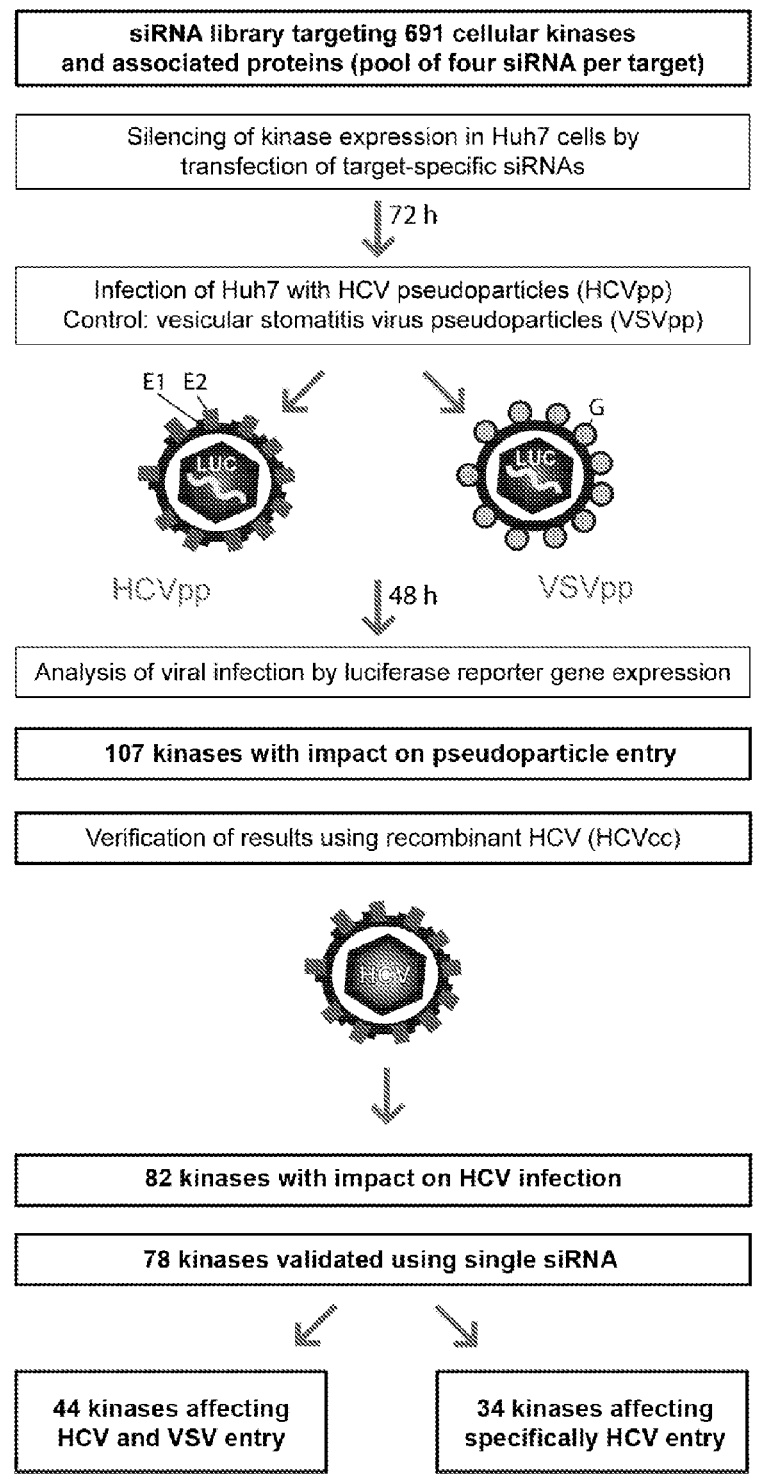
FIG. 4 shows a schematic outline of the functional RNAi HCVpp entry screen used, in the second experiment, to identify host cell-derived HCV entry cofactors. Details of the screens are given in Example 2.

2. Identification of Cellular Kinases Involved in HCV Entry Using a Genome-Wide RNAi Kinase HCV Entry Screen An siRNA-based screen was performed silencing 691 human kinases in Huh7 cells to comprehensively identify all the cellular kinases in the human genome that might be associated with HCV entry. Defects in the later stages of infection such as replication, assembly or secretion were not addressed in this assay. The readout of the assay comprised of infection of gene-silenced cells with HCVpp or HCVcc containing a luciferase reporter. This was followed by quantification of viral entry by assaying reporter gene expression 72 hours after infection. Screening involved three steps: a primary screen using HCVpp side-by-side with pseudotyped particles derived from vesicular stomatitis virus (VSPpp) serving as an unrelated control virus. To validate the relevance of the identified hits for the infectious viral life cycle, hits identified in the primary screens were confirmed in a secondary screen using an infectious HCV cell culture model based on recombinant HCVcc and Huh7.5.1 cells (FIG. 4). Primary and secondary screens were performed using pools of four siRNAs targeting the same gene. Candidate genes from the secondary screen were subjected to a third round of screening in which the four component siRNAs in each pool were individually rescreened (FIG. 4).

In summary, 107 kinases were identified by the primary HCVpp screen, and of these, 82 were validated by infection with recombinant HCVcc. This differential could be due to the fact that the entry mechanisms of HCVpp and HCVcc may differ in subtle ways. Alternatively, some kinases may subsequently have antagonistic effects on post-entry events in the HCV life cycle, such as replication. This is illustrated by the finding that silencing of NEK4 kinase, which has been shown to enhance replication (Tai, 2009), enhanced HCVcc infection but inhibited the entry of HCVpp (data not shown). Seventy-eight (78) of the 82 kinases (95%) with a similar effect on HCVpp entry and initiation of HCVcc infection were validated by individual siRNAs (FIG. 10), demonstrating that it was indeed gene silencing rather than off-target effects of individual siRNA sequences that caused the observed phenotype.

Figure 10:
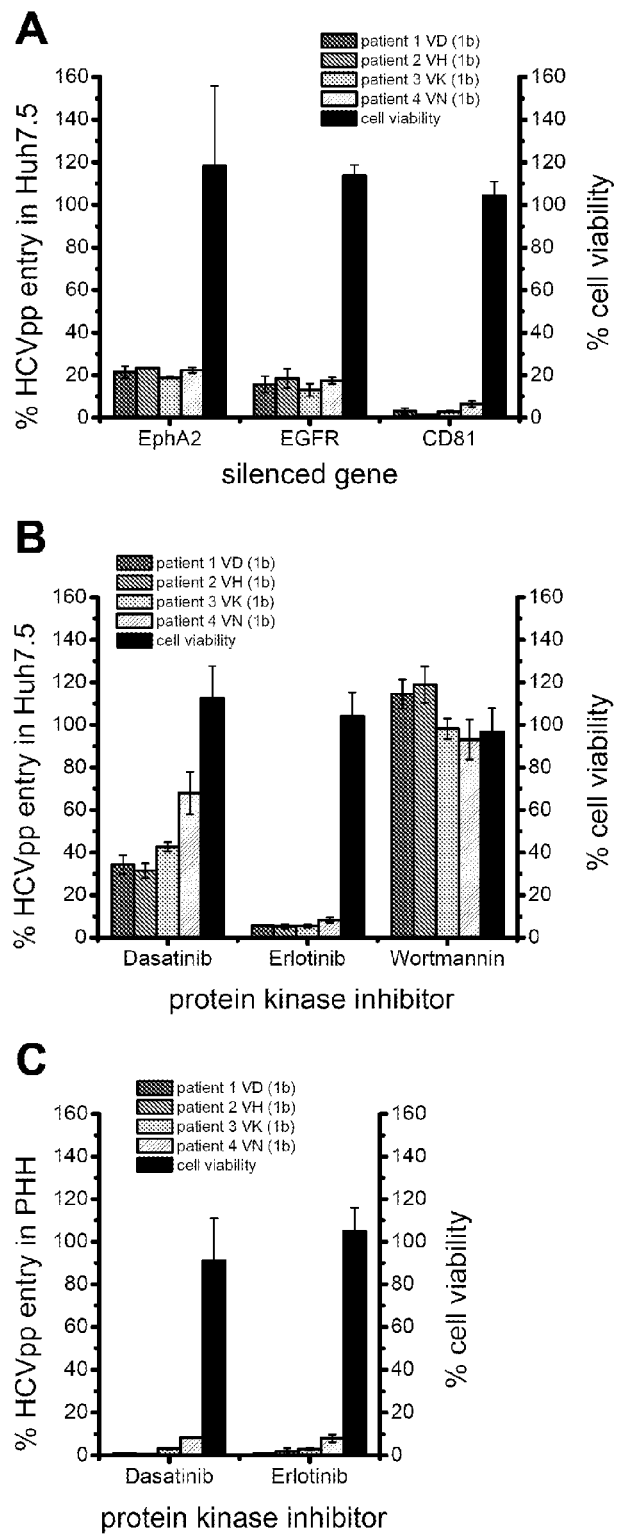
FIG. 10 demonstrates that the targeting of host cell kinases with multikinase inhibitors results in inhibition of infection of HCV isolates derived from patients undergoing liver transplantation. HCVpp (genotype 1b) bearing envelope glycoproteins from HCV strains VD, VH, VK, VN isolated during liver transplantation from four different HCV-infected patients. Entry of all strains was inhibited by gene silencing using specific individual siRNAs targeting EphA2, EGFR or CD81 in Huh7.5 (A) and by treatment of Huh7.5 cells (B) or primary human hepatocytes (PHH) (C) with Dasatinib or Erlotinib 1 hour prior to infection at a concentration of 10 μM. In contrast, Wortmannin (10 μM) did not inhibit HCVpp entry. Cell viability was not reduced by either gene silencing (as compared to a non-specific control siRNA) or inhibitor treatment (compared to a solvent control) (B-C). Data are expressed as percent HCVpp entry or cell viability of CTRL siRNA-transfected cells or solvent control-treated cells (CTRL=100%; mean±SD are shown).

Thus, the genome-wide, RNAi kinase screen identified 78 kinases with impact on HCV entry and initiation of HCV infection as confirmed in an infectious cell culture model (FIG. 10). To identify kinases which may be specifically involved in HCV entry, the effect of silencing on entry of an unrelated control virus, VSV was studied. Using this side-by-side analysis, 34 genes were identified that had a functional impact on HCVpp entry and HCVcc infection but no effect on VSV entry (FIG. 10A).

The validity of this RNAi screening method is confirmed by the identification of kinases that are known to be essential for the entry of control virus VSV. A comparative analysis of hits for VSVpp entry identify in the primary screen and in the screen performed by Pelkmans and coworkers (Pelkmans, 2005) confirmed the functional relevance of kinases involved in clathrin-mediated viral endocytosis for HSV entry. Furthermore, the primary HCVpp screen confirmed the relevance of protein kinase A for HCVpp entry as shown recently by Farquhar et al. (Farquhar, 2008). The identification of these kinases as co-host factors for VSV and HCV entry confirms the validity of the present screening approach.

3. Identification of Kinase Networks Involved in HCV Entry by Bioinformatic Analysis To obtain a classification of the known physiological functions of the identified kinases and associated proteins, a bioinformatic analysis using the Ingenuity Pathways data was performed as described for other RNAn siRNA-based screens (Krishnan, 2008 and Tuvim, 2009). This analysis revealed a high representation of genes involved in cancer and cell death (FIG. 6A). When classifying kinases with an impact on HCV but not on VSV entry, the five most highly represented categories included: amino acid metabolism, post-translational modification, small molecule biochemistry, cell morphology, cellular development, cell cycle, cell signalling, and cancer (FIG. 6B).

Next, the identified hits were analyzed for known and predicted protein interaction using the STRING database (Jensen, 2009). The interactions addressed included direct (physical) or indirect (functional) associations derived from numerous sources, including experimental repositories, computational prediction methods and public text collections (Jensen, 2009). STRING represents a meta-database mapping of all known protein-protein interactions onto a common set of genomes and proteins. Analysis of the 78 kinases identified in the RNAi screen revealed kinase networks regulating cell morphology including cell polarity, tight junction permeability, and integrin signalling, as well as networks of kinases involved in the cell cycle (FIG. 6C).

a) Host Cell Kinases Regulating Cell Polarity.

Figure 7:
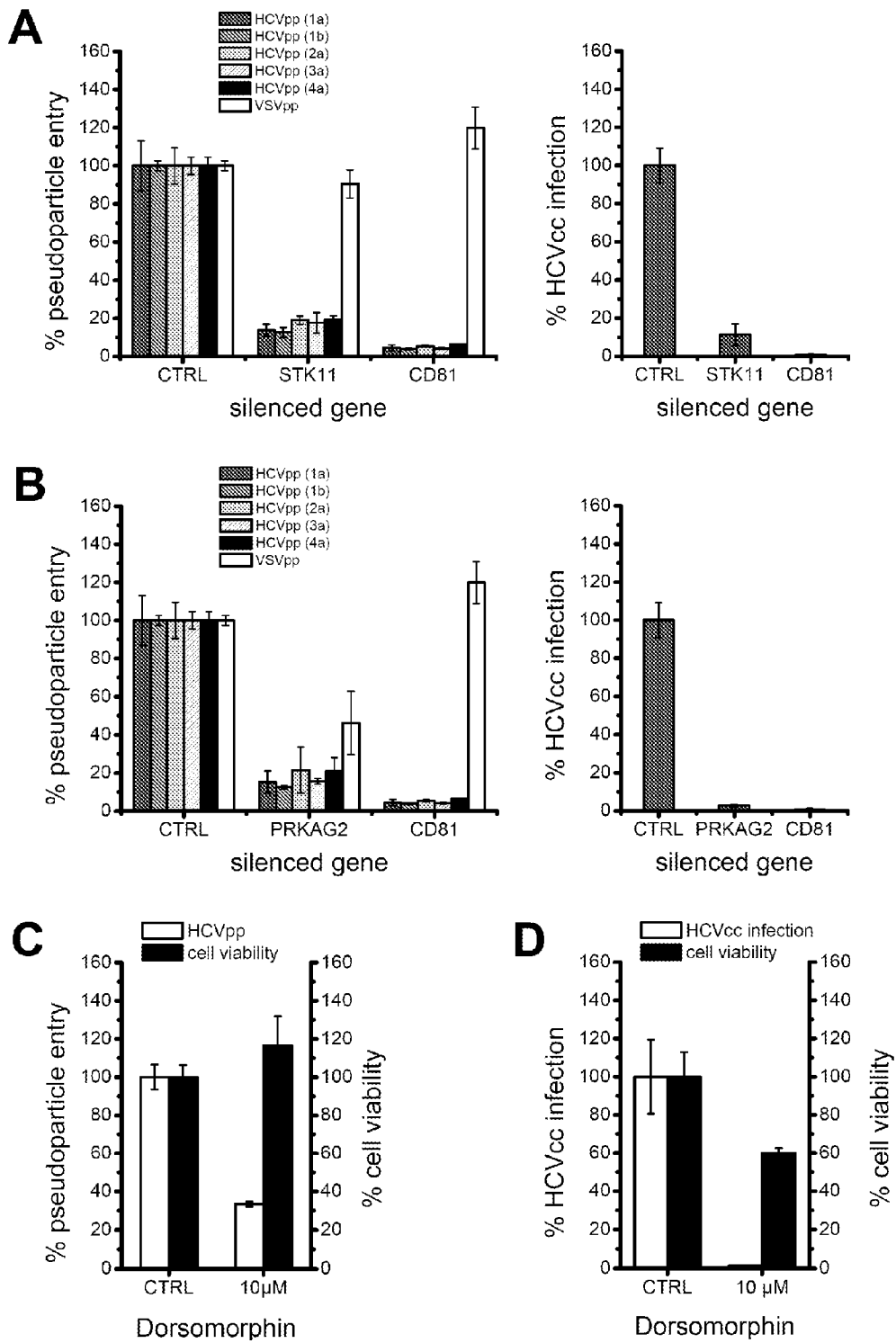
FIG. 7 demonstrates that silencing of liver kinase B1 (STK11) and AMP-activated protein kinase subunit gamma 2 (PRKAG2) expression results in inhibition of HCVpp entry and HCVcc infection (see Example 2). Silencing of STK11 (A) or PRKAG2 (B) by specific individual siRNAs in Huh7.5 cells resulted in inhibition of the entry of HCVpp derived from genotypes 1a, 1a, 2a, 3a, and 4a (left panel), and HCVcc infection (HCVcc Luc-Jc1; genotype 2a/a2) (right panel). In contrast, control siRNA transfection (CTRL) did not affect HCV infection. Inhibition of AMPK activity by protein kinase inhibitor Dorsomorphin inhibited HCVpp entry (HCVpp H77C; genotype 1a) in Huh7.5 cells (C) and HCVcc infection (HCVcc Luc-Jc1; genotype 2a/2a) in Huh7.5.1 cells (D). Cell viability was not diminished in Huh7.5 cells but slightly reduced in Huh7.5.1 (as shown by MTT assay) (C-D). Cells were pretreated for 1 hour and treated during infection for 6 hours with 10 μM Dorsomorphin. Data are expressed as percent HCVpp entry, HCVcc infection, or cell viability of CTRL siRNA-transfected cells or solvent control-treated cells (CTRL=100%; mean±SD are shown).

First, RNAi screening with subsequent STRING analysis identified: liver kinase B1 (STK11) and AMP-activated protein kinase (AMP, γ2 non-catalytic subunit PRKAG2) as host factors for HCV entry (FIG. 6-7). The PRKAG2 subunit serves as an activator for AMPK. As shown in FIG. 7, silencing of the expression of the genes for STK11 or the AMPK subunit PRKAG2 led to a marked inhibition of entry of HCVpp derived from all major genotypes (FIG. 7A-B, left panels). Similar results were obtained for infection with recombinant HCV suggesting that the identified kinases are important for initiation of a productive infection (FIG. 7A-B, right panels). In contrast, incubation of cells with a control siRNA did no significantly modify HCV entry or HCV infection (FIG. 7). Silencing of two corresponding inhibitory AMPK subunits, namely β1 (PRKAB1) and β2 (PRKAB2), stimulated HCVpp entry suggesting that AMPK activity is crucial for HCV entry and infection. The impact of this pathway was further confirmed by the use of Dorsomorphin, an inhibitor of AMPK activity (Zhou, 2001). Preincubation of Huh7.5 cells with Dorsomorphin markedly inhibited HCVpp entry (FIG. 7C) and confirmed that the AMPK function is indeed important for HCV entry.

STK11 and its downstream substrate AMPK have been shown to play a major role in the establishment of polarity in epithelial cells, including hepatocytes (Williams, 2008). Other studies suggest that AMPK mediates the polarity- and mitosis-controlling functions of STK11 (Lee, 2007). This is of particular interest for HCV entry because cell polarity has been shown to be an important host factor for HCV entry (Brazzoli, 2008; Evans, 2007; Mee, 2008; Meertens, 2008; Ploss, 2009). Cell polarity appears to alter the subcellular localization of HCV entry factor claudin-1 and to modulate viral entry in HepG2 hepatoma cells (Mee, 2009). Furthermore, Brazzoli and coworkers (Brazzoli, 2008) have shown that the binding of HCV E2 glycoprotein to CD81 triggers an actin-dependent re-localization of the HCV E2/CD81 complex to cell-cell contact areas where CD81 comes into contact with the tight junction proteins occluding, ZO-1, and claudin-1. Inhibition of AMPK by Dorsomorphin has been shown to block phosphorylation of non-muscle myosin regulatory light chain (MRLC) (Lee, 2007). Taken together, these results support a model in which STK11/AMPK function could be required for actin-myosin-dependent transport or trafficking of the HCV-entry factor complexes on the cell surface or within the cell (FIG. 6D).

b) Host Cell Kinases Regulating Tight Junction Function.

The RNAi screen identified several kinases involved in regulation of tight junction (TJ) function. These include MAGI-1, EphA2 and EGFR (FIG. 6C). In polarized hepatocytes TJ separate their plasma membrane into apical and basolateral domains. This is of interest and of relevance for HCV entry since several TJ proteins, namely claudin-1, 6 and 9 (Evans, 2007; Harris, 2008; Meertens, 2008) and occluding (Benedicto, 2009; Ploss, 2009), have been shown to be cofactors for HCV entry. The use of several uptake factors with distinct cell surface distributions is consistent with the hypothesis that HCV could follow a coordinated entry pathway similar to that of Coxsackievirus B, which is dependent on the hepatocyte TJ (Ploss, 2009). Alternatively, HCV may utilize forms of claudin-1 that are not associated with TJs (Mee, 2009). Disrupting TJ has been shown to enhance HCV entry in CaCo-2 cells, supporting a model in which TJ provide a physical barrier for viral access to HCV entry factors expressed on lateral and basolateral cellular domains (Mee, 2008).

Figure 8:
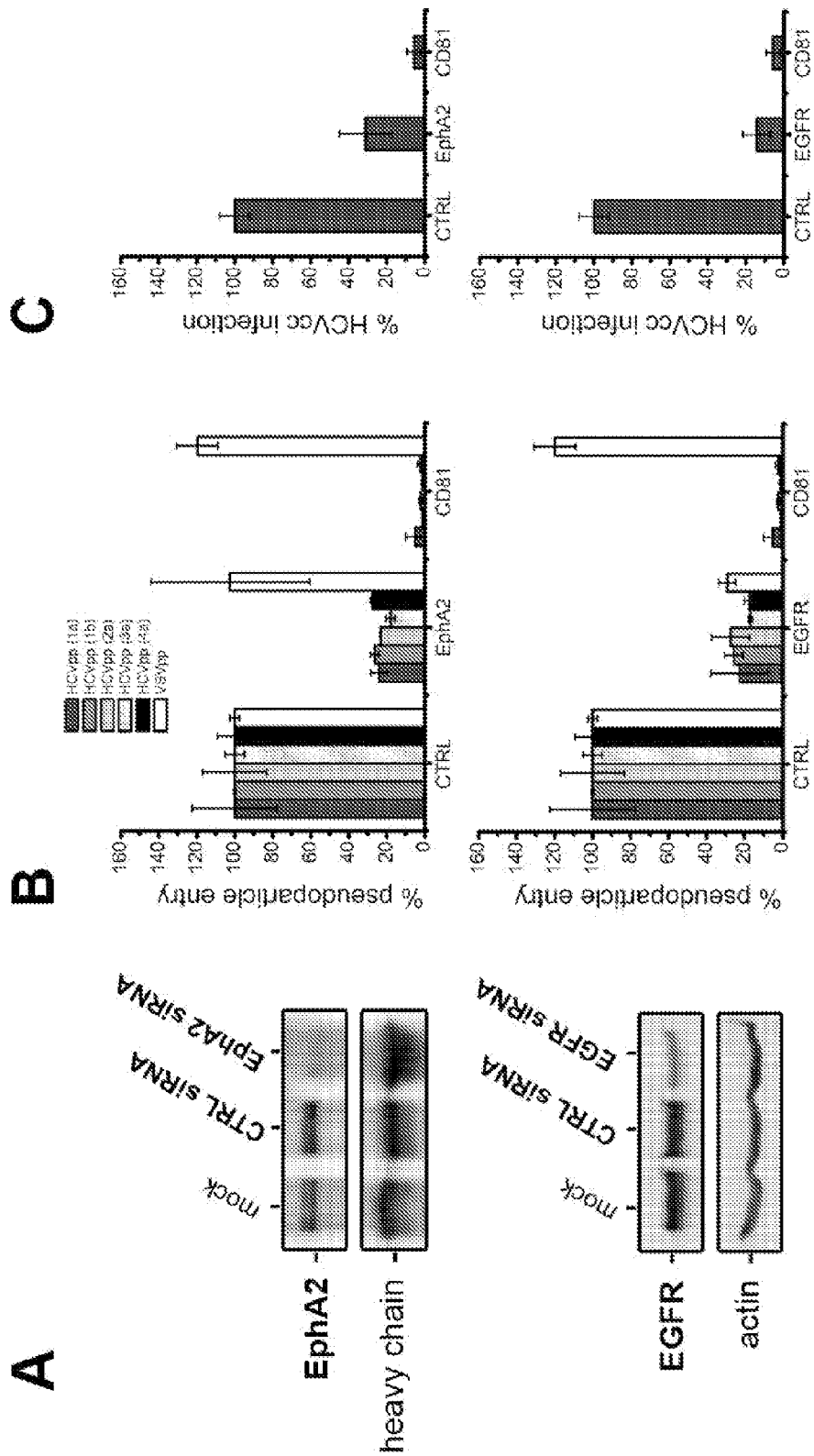
FIG. 8 demonstrates that silencing of EphA2 and EGFR expression in human hepatoma cells results in genotype-independent inhibition of HCVpp entry and HCVcc infection. (A) Silencing of EphA2 or EGFR gene transcription in Huh7.5 cells using individual siRNAs results in reduced expression of the corresponding protein. Expression is compared to cells transfected with a control siRNA (CTRL) as shown by immunoprecipitation and western blotting. Mock=untreated cells. (B) Silencing of EphA2, EGFR or CD81 expression by specific individual siRNAs resulted in inhibition of the entry of HCVpp derived from genotypes 1a, 1b, 2a, 3a, and 4a. In contrast to EGFR, EphA2 silencing had no effect on the entry of VSVpp control particles. (C) Silencing of EphA2, EGFR or CD81 expression by individual siRNAs resulted in marked inhibition of HCVcc infection (HCVcc Luc-Jc1, genotype 2a/2a). In contrast, control siRNA transfection (CTRL) did not affect HCV infection. Data are expressed as % HCVpp entry or HCVcc infection of CTRL-siRNA transfected cells (CTRL=100%; mean±SD are shown).

MAGI-1 is a membrane-associated guanylate kinase involved in the formation of junction complexes (Laura, 2002). Ephrin receptor A2 (EphA2) is a member of the largest class of receptor tyrosin kinases and mediates cell positioning, cell morphology and mobility as well as paracellular TJ permeability (Lackmann, 2008). As shown in FIG. 8, silencing of EphA2 gene expression (FIG. 8A) led to a marked inhibition of the entry of HCVpp derived from all major genotypes 1-4 (FIG. 8B), and infection with recombinant HCV suggesting that the identified kinase is important for initiation of a productive infection (FIG. 8C). In contrast, incubation of cells with a control siRNA (CTRL) did not significantly modify HCV entry or HCV infection (FIG. 8). The impact of this pathway was further confirmed by the use of Dasatinib, an inhibitor of EphA2 function (Huang, 2007). Preincubation with Dasatinib markedly inhibited HCVpp entry in primary human hepatocytes and HCVcc infection of Huh7.5.1 cells (FIG. 9) and confirmed that EphA2 function is indeed important for HCV entry. EphA4 has been shown to mediated paracellular permeability in endothelial tissue by g TJ protein claudin-4 (Tanaka, 2005).

Figure 9:
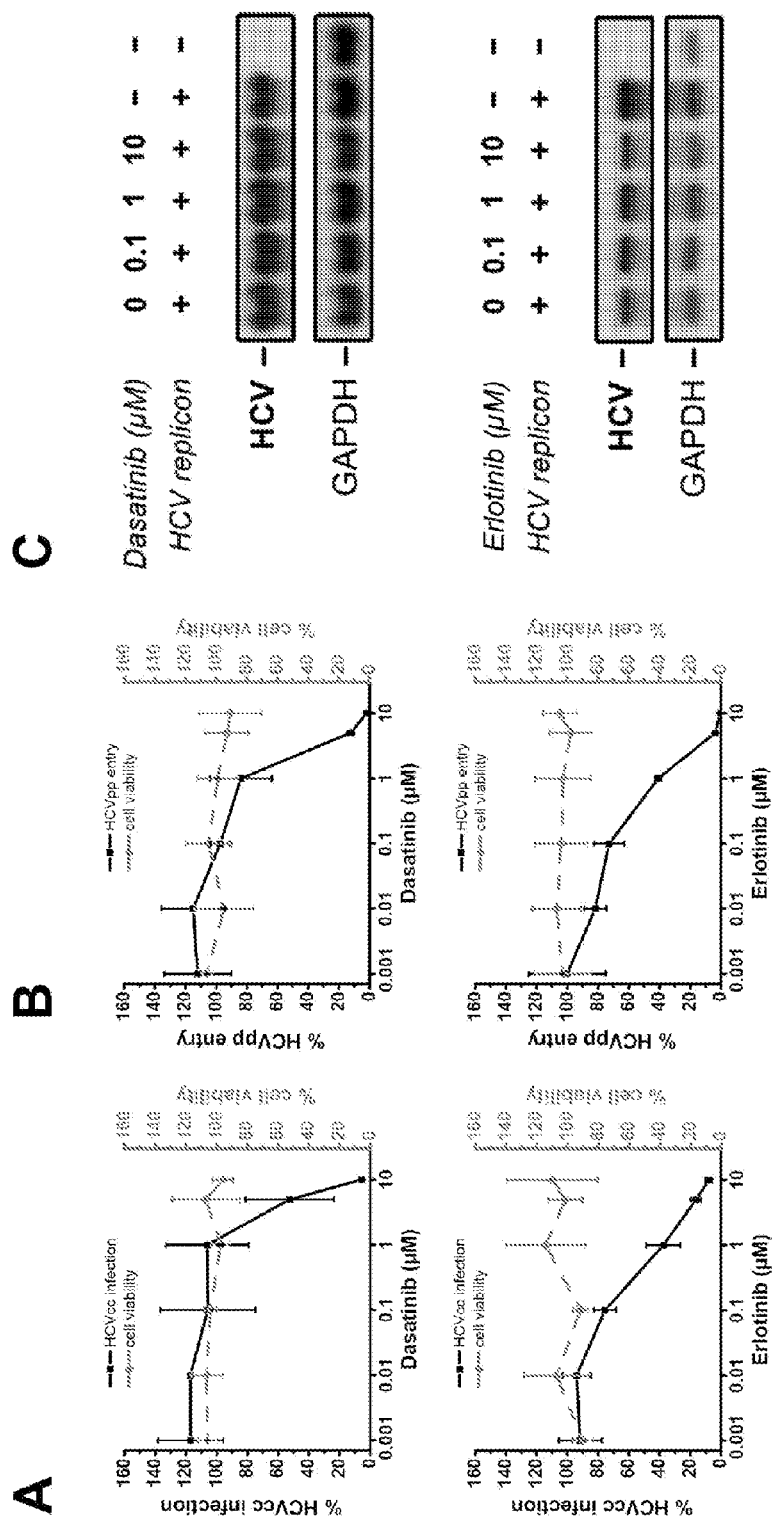
FIG. 9 shows the dose-dependent inhibition of HCVcc infection and HCVpp entry by the protein kinase inhibitors Dasatinib and Erlotinib. Following incubation with Dasatinib or Erlotinib, HCVcc infection (HCVcc Luc-Jc1, genotype 2a/2a) of Huh7.5 cells (A) and HCVpp entry in primary human hepatocytes (HCVpp JFH1; genotype 2a) (B) was assessed by luciferase reporter gene expression. Dasatinib and Erlotinib inhibited HCVcc infection (A) and HCVpp entry in primary human hepatocytes (B) in a dose-dependent fashion. Kinase inhibitors were added 1 hour prior to infection. Viability of treated cells was assessed using a MTT assay and is shown as dashed grey lines. Data are expressed as percent HCVcc infection or HCVpp entry vis-à-vis solvent-treated control cells (CTRL=100%; mean±SD are shown). (C) Dasatinib and Erlotinib did not inhibit HCV replication as percent HCVcc replication. Huh7.5 cells were transfected with HCV RNA from the subgenomic HCV JFH1 replicon as described in Example 2. Four hours following electroporation, the cells were incubated for 24 hours with solvent CTRL, Dasatinib or Erlotinib. HCV RNA and GAPDH RNA were analyzed by Northern blotting.

Furthermore, epidermal growth factor receptor (EGFR) was identified as a cofactor for HCV entry. As shown in FIG. 8, silencing EGFR expression (FIG. 8A) led to a marked inhibition of the entry of HCVpp derived from all major genotypes 1-4 (FIG. 8B) as well as infection with recombinant HCV. These findings suggest that this kinase is important for initiation of a productive infection (FIG. 8C). Like EphA2, EGFR is a tyrosine kinase receptor regulating key processes of cell biology, including proliferation, survival, differentiation, during development, tissue homeostasis, and tumorigenesis (Schneider and Wolf, 2009). In vivo, EGFR mainly activates Raf/MEK/ERK and PI3K/Akt signaling (Lackmann, 2008; Schneider, 2009). Interestingly, the primary screen used demonstrated also that silencing of kinases mediating EGFR signaling markedly inhibited HCV entry: these include b-Raf (BRAF), MEK1 (MAP2K1), and ERK1 (MAPK3) (FIG. 6D). The relevance of the Raf/MEK/ERK pathway for HCV entry is further supported by the use of defined inhibitors inhibiting EGFR as well as downstream kinases of EGFR Inhibition of EGFR activity using Erlotinib dose-dependently inhibited HCV entry and HCV infection (FIG. 9). In contrast, inhibiting PI3K activity using Wortmannin (Arcaro, 1993) did not (FIG. 10B). The relevance of the Raf/MAK/ERK signaling pathway for HCV entry is further supported by a recent study showing that CD81 engagement activates the Raf/MAK/ERK signaling cascade and that this pathway affects post-entry events of the virus life cycle (Brazzoli, 2008). Taken together, these data support a model in which EGFR activation and signaling via the MAP-kinase pathway is required for HCV entry.

What is the molecular function of EGFR during the HCV entry process? EGFR activation has been shown to induce cellular redistribution and increased expression of claudin-1 (Flores-Benitez, 2007; Singh, 2004) and EGF-mediated MAP-kinase signaling has been shown to result in an interaction of MAP-kinase ERK-1 with a C-terminal region of occludin, which prevents $H_2O_2$-induced disruption of tight juntions by EGF (Basuroy, 2006). Taken together, these data and the results of the present RNAi screen further support a functional role of TJ proteins for HCV entry and demonstrate a functional link between EGFR with TJ proteins claudin-1 or occludin mediated by the MAP-kinase pathway (FIG. 6D).

It is of interest to note that expression of HCV nonstructural proteins has been shown to result in up-regulation of EphA2 and EGFR expression. Indeed, HCV non-structural protein NS4B has been shown to cause a concomitant increase in the total levels of EphA2 (Zheng, 2005). NS5B has been shown to result in an increase in EGFR expression and an alteration of the trafficking profile of EGFR (Mankouri, 2008). The authors of this study had suggested that MAP-kinase signaling might maintain an optimal environment for HCV persistence (Mankouri, 2008). Taken together, these data and the results of the present RNAi screen suggest a positive feed-back loop where HCV replication and expression of non-structural proteins NS4B and NS5A results in up-regulation of HCV co-entry factors EphA2 and EGFR thereby facilitating HCV entry and viral propagation.

c) Host Cell Kinases Involved in Integrin Signaling.

STRING analysis identified a network of four kinases involved in cell adhesion and integrin signalling: c-Src (CSK), focal adhesion kinase (PTK2), focal adhesion kinase 2 (PTK2B), and integrin-linked kinase (ILK), all of which regulate cell adhesion and cell-matrix interaction (D Nichila, 1999; Harburger, 2009) (FIG. 6C). It has been shown that CD81, a key HCV entry factor, and other tetraspanins are associated with adhesion receptors of the integrin family and regulate integrin-dependent cell migration (Berditchevski, 2001). It is thus conceivable that functional integrin signalling might be a prerequisite for HCV entry factor trafficking and localization on the cell surface, and therefore for HCV entry. In this context a number of tetraspanins, including CD81, are associated with type II phosphatidylinositol 4-kinase and it is suggested that this may facilitate the assembly of signalling complexes by tethering these enzymes to integrin heterodimers (Berditchevski, 2001). This is supported by the present finding that silencing of phosphatidylinositol 4-kinase type 2 alpha (PI4KII) specifically impaired HCV entry and infection but did not affect VSV entry. Moreover, it is known that integrin signalling plays a pivotal role in the entry of other viruses such as adenovirus, hantavirus and herpesviruses (for a review see Stewart, 2007): HCV may therefore have another integrin-dependent entry mechanism.

d) Host Cell Kinases Involved in Cell Cycle.

STRING analysis pointed to a network that included 8 kinases involved in cell cycle regulation (FIG. 6C) including cell division cycle 2 kinase (CDC2), cyclin-dependent kinase 3 (CDK3), cyclin-dependent kinase 4 (CDK4), cholin kinase alpha (CHKA), cyclin-dependent kinase inhibitor 1B (CDKN1B), cyclin-dependent kinase inhibitor 2C (CDKN2C), membrane associated tyrosine/threonine protein kinase 1 (PKMYT1), and WEE1 homolog S. pombe (WEE1). Although the possibility cannot be excluded that these CDKs were identified because of intrinsic properties of the cell division-dependent hepatoma model system, several observations support a specific role of CDKs for HCV entry. Firstly, silencing of CDK3 markedky inhibited entry of HCVpp derived from all major HCV genotypes 1-4 but not of VSVpp. A specific effect on HCV entry was also observed when CDKN1B, CDKN2C, WEE1 and PKMYT1 were silenced. Secondly, after gene silencing (apart from experiments with CHKA), no cytotoxicity was observed as measured by the cellular metabolization of MTT. This suggests that the silencing of kinases was not due to non-specific toxic effects. Thirdly, Flavopiridol, a well-characterized CDK3 inhibitor, markedly inhibited HCVpp entry in the absence of any detectable cytotoxic effects in primary human hepatocytes. These data suggest that the effect of CDKs is not related to either the model target cell line or the pseudoparticle entry assay, and could be relevant to HCV entry. It is well known that CDKs play an important role in the life cycle of human immunodeficiency and herpes viruses. These include regulation of HIV transcription by CDK9 (Zhou, 2009) and the activation by Kaposi sarcoma-associated herpes virus of CDK4 and CDK6 that regulate microfilament organization and cell morphology (Cuomo, 2005). Thus, it is conceivable that similar mechanisms apply for HCV.

4. Confirmation of the Specific Impact of Identified Kinases on HCV Entry by Inhibition of Host Cell Kinases by Defined Inhibitors To further study the impact of the identified kinases on the HCV life cycle, the functional impact of EphA2 and EGFR was characterized. These kinases were selected because they are components in networks identified (FIG. 6C). Furthermore, EphA2 and EGFR are potently inhibited by the clinically approved kinase inhibitors Dasatinib (for EphA2) and Erlotinib (for EGFR), making it possible to investigate the functional impact of these kinases at different stages of the viral life cycle. The effect of kinase inhibitors on HCV entry, replication and infection was studied. As shown in FIG. 9, Dasatinib and Erlotinib markedly inhibited HCV infection. Erlotinib was the most potent inhibitor of HCV entry and infection ($IC_{50}$ approximately 0.5 µM), followed by Dasatinib (IC50 2 µM). The observed $IC_{50}$ values were higher than the described $IC_{50}$ values of purified EphA2 (Huang, 2007) or EGFR (Minami, 2007). The higher $IC_{50}$ values observed in hepatocytes or hepatocyte-derived cell lines are probably due to rapid metabolism of the inhibitor in hepatocytes or hepatoma cells. Nevertheless, the possibility cannot be excluded that additional kinases contribute to the antiviral impact of Dasatinib and Erlotinib but, in the case of EGFR, the present results (FIG. 9) were confirmed with three additional EGFR inhibitors (Gefitinib, Vandetanib, Lapatinib) that inhibited HCV infection at a similar $IC_{50}$ (not shown). The inhibitory effect of Dasatinib and Erlotinib on HCVcc infection was confirmed by detection of viral RNA using RT-PCR excluding a non-specific impact of the drugs on translation of the luciferase reporter (data not shown).

To confirm that the inhibitory effect of these molecules on HCV infection was indeed on viral entry, their effect on the entry and replication of HCV isolate JFH1 was studied. As shown in FIG. 9, Dasatinib and Erlotinib inhibited JFH1-derived HCVpp entry without markedly modulating replication of the subgenomic JFH1 replicon. In contrast, Wortmannin, a protein kinase inhibitor that inhibits viral replication (Tai, 2009), did not have any effect on JFH1-derived HCVpp entry (data not shown). These data confirm that kinases that are selectively inhibited by Dasatinib and Erlotinib are important in HCV entry but not in viral replication. These findings further confirm that kinases that are selectively inhibited by Dasatinib and Erlotinib are important in HCV entry but not in viral replication. These findings further confirm the impact of the identified kinases for HCV entry and suggest that inhibiting host kinases using approved compounds may be a useful therapeutic strategy against HCV.

5. Inhibition of Entry of HCV Isolates Derived from Patients Undergoing Liver Transplantation by Targeting Host Cell Kinases Using Multikinase Inhibitors Since Erlotinib potently inhibited HCV entry and infection in a dose range ($IC_{50}$ 0.5 µM) corresponding to achievable plasma concentrations (mean plasma concentrations ~4 µM, Hidalgo and Bloedow, 2003), its affect was assessed on infection with patient-derived isolates. Using primary human hepatocytes and HCV pseudotypes bearing viral envelope glycoproteins derived from four HCV-infected patients undergoing liver transplantation, the present Applicants have demonstrated that enhanced viral entry and escape from antibody-mediated neutralization are key determinants for selection of viral variants during HCV re-infection of the liver graft (Fafi-Kremer, 2009). The results of this previous study have suggested that viral entry is a viable target for prevention of HCV re-infection of the liver graft (Fafi-Kremer, 2009). In the present study, the effect of multikinase inhibitors was studied on the entry of HCVpp bearing envelope glycoproteins from HCV strains selected during transplantation and re-infecting the liver graft in four different patients (HCV strains VD, VH, VK, VN). As shown in FIG. 9, silencing of identified host cell kinases as well as pre-incubation of cells with kinase inhibitors Dasatinib and Erlotinib markedly inhibited entry of patient-derived HCVpp in Huh7.5 cells and in primary human hepatocytes. Erlotinib appeared to be more potent than Dasatinib in Huh7.5 cells but not in primary human hepatocytes. In contrast, Wortmannin (FIG. 10) or a naphthyridine-based TpI2 kinase inhibitor (data not shown) did not result in a reproducible inhibition of HCVpp infection. These data suggest that Erlotininb and Dasatinib specifically inhibit HCV entry of patient-derived isolates infecting the liver graft. No toxic effects were detected in a side-by-side analysis of cell viability based on MTT testing (FIG. 10).

Taken together, these results suggest that host cell kinases that regulate HCV entry are a viable target for antiviral therapy. The clinical development of protein kinase inhibitors offers a new perspective for antiviral strategies based on the targeting of specific, host cell kinases that are required for viral infection. Since this approach is complementary to antiviral strategies targeting viral proteins, it may represent a valuable way of overcoming viral resistance. Moreover, inhibition of HCV entry using licenced kinase inhibitors may constitute a novel therapeutic approach to preventing primary HCV infection, notably after liver transplantation, and might also attenuate virus spread in chronically infected patients.

REFERENCES

D. B. Allison et al., Nat. Rev. Genet., 2006, 7: 55-65.
A. Arcaro et al., Biochem. J., 1993, 296 (2), 297-301.
H. Barth et al., J. Biol. Chem., 2003, 278: 41003-41012.
H. Barth et al., J. Virol., 2006, 80: 10579-10590.
H. Barth et al., Hepatology 2006, 44:527-35.
H. Barth et al., J. Hepatol., 2008, 49:134-42.
B. Bartosch et al., J. Exp. Med., 2003, 197: 633-642.
S. Basuroy, Biochem. J., 2006, 393: 69-77.
I. Benedictor et al, J. Virol., 2009, 83: 8012-8020.
F. Berditchevski et al, J. Cell. Sci., 2001, 114:4143-4151.
M. Brazzoli et al., J. Virol., 2008, 82, 8316-8329.
R. S; Brown, Nature, 2005, 436: 973-978.
M. A Cirone et al., Int. J. Cancer, 1990, 45: 490-493.
F. V. Chisari, Nature, 2005, 435: 930-932.
S. N. Constantinescu et al., FEBS Lett., 1991, 292: 31-33.
M. E. Cuomo, J. Biol. Chem., 2005, 280: 35844-35858.
P. David et al., Hum. Exp. Toxicol., 1998, 17: 544-553.
M. O De Nichilo et al., J. Cell Physiol., 1999, 178: 164-172.
M. Dimitova et al., PNAS, USA, 2008, 105: 16320-16325.
M. J. Evans et al., Nature, 2007, 446: 801-805.
S. Fafi-Kremer et al., "Escape from antibody-mediated neutralization and viral entry are key determinants for HCV re-infection in liver transplantation", 2009, submitted.
X. Fang et al., Hepatology 2006, 43:1326-36.
M. J. Farquhar et al., J. Virol., 2008, 82: 8797-8811.
J. J. Feld et al., Nature, 2005, 436: 967-972.
D. Flores-Benites et al., Am. J. Physiol. Renal. Physiol., 2007, 292: F828-836.
R. C Gentleman et al., Genome Biol., 2004, 5: R80.
D. S. Harburger et al., J. Cell. Sci., 2009, 122: 159-163.
H. J. Harris et al., J. Virol., 2008, 82: 5007-5020.
M. Hildago et al., Semin. Oncol., 2003, 30: 25-33.
J. H. Hoofnagle, Hepatology, 2002, 36: S21-S29.
F. Huang et al., Cancer Res., 2007, 67: 2226-2238.
M. Hsu et al., Proc. Natl. Acad. Sci. USA, 2003, 100: 7271-727.
F. Huang et al., Cancer Res., 2007, 67: 2226-2238.
J. L. Jensen et al., Nucleic Acids Res., 2009, 37, D412-416.
T. Kato et al., J. Virol., 2005, 79:592-6.
T. Kato et al., J. Virol., 2007, 81: 4405-4411.
T. Kato et al., Hepatology, 2008, 48:732-40.
G. Koutsoudakis et al., J. Virol., 2006, 80: 5308-5320.
M. N. Krishnan et al, Nature, 2008, 455: 242-245.
M. Lackmann et al., Sci. Signal., 2008, 1: re2.
L. Lan et al., J. Immunol., 2008, 181: 4926-4935.
G. M. Lauer et al., N. Engl. J. Med., 2001, 345: 41-52.
R. P. Laura et al., Exp. Cell. Res., 2002, 275: 155-170.
M. Law et al., Nat. Med., 2008, 14: 25-7.
J. H. Lee et al., Nature, 2007, 447, 1017-1020.
B. D. Lindenbach et al., Science, 2005, 309: 623-626.
B. D. Lindenbach et al., Proc. Natl. Acad. Sci. USA, 2006, 103: 3805-3809.
V. Lohmann et al., Science, 1999, 285: 110-113.
J. Mankouri et al., Traffic, 2008, 9: 1497-1509.
C. J. Mee et al., J. Virol., 2008, 82, 461-470.
C. J. Mee et al., J. Virol., 2009, 83, 6211-6221.
L. Meertens et al., J. Virol., 2008, 82, 3555-3560.
J. C. Meunier et al., J. Virol., 2008, 82: 966-973.
D. F. Mercer et al., Nat. Med., 2001, 7:927-33.
Y. Minami et al., Oncogene, 2007, 26: 5023-5027.
T. Mosmann et al., J. Immunol. Methods, 1983, 65: 55-63.
J. M. Pestka et al., PNAS, USA, 2007, 104: 6025-6030.
Pawlotsky, Trends Microbiol., 2004, 12: 96-102.
L. Pelkmans et al., Nature, 2005, 436: 78-86.
J. M. Pestka et al., Proc. Natl. Acad. Sci. U.S.A., 2007, 104: 6025-6030.
T. Pietschmann et al., PNAS, USA, 2006, 103: 7408-7413
P. Pileri et al., Science, 1998, 282: 938-941.
C. N. Root et al., J. Gen. Virol., 2000, 81: 2697-2705.
A. Ploss et al., Nature, 2009, 457: 882-886.
M. R. Schneider et al., J. Cell. Physiol., 2009, 218: 460-466.
L. B. Seeff, Semin. Gastrointest., 1995, 6: 20-27.
L. B. Seeff and J. H. Hoofnagle, Hepatology, 2002, 36: 1-2.
E. Scarselli et al., EMBO J., 2002, 21: 5017-5025.
S. B. Sieczkarski et al., J. Virol., 2003, 77: 460-469.
A. B. Singh et al., J. Biol. Chem., 2004, 279: 3543-3552.
A. S. Smith et al., Science 2004, 304:237-42.
P. L. Stewart et al., Trends Microbiol., 2007, 15: 500-507.
K. Strimmer, Bioinformatics, 2008, 24: 1461-1462.
A. W. Tai et al., J. Hepatol., 2009, 50: 412-420.
M. Tanaka et al., J. Biol. Chem., 2005, 280: 42375-42382.
A. W. Tan et al., Hepatology, 2006, 43: 592-601.
M. J. Tuvim et al., PLoS ONE, 2009, 4, e4176.
T. Vanwolleghem et al., Gastroenterology, 2007, 133:1144-55.
T. Wakita et al., Nat. Med., 2005, 11: 791-796.
J. M. Wettenhall et al., Bioinformatics, 2004, 20: 3705-3706.
T. Williams et al., Trends Cell. Biol., 2008, 18, 193-198.
M. B. Zeisel et al., Hepatology, 2007, 46: 1722-1731.
M. B. Zeisel et al., Hepatology, 2008, 48: 299-307
Y. Zheng et al., J. Biochem. Mol. Biol., 2005, 38: 151-160.
G. Zhou et al., J. Clin. Invest., 2001, 108, 1167-1174.
M. Zhou et al., J. Virol., 2009, 83: 1036-1044.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for identifying a potential HCV anti-viral agent comprising steps of:
   (a) contacting in vitro a biological system that expresses at least one human cellular protein kinase with a candidate compound, wherein the protein kinase is selected from the group consisting of EGFR, EPHA2, FGR, AURKB, BRAF, EPHA3, EPHB1, FGFR4, ERBB4, LTK and BMP2K; and
   (b) determining the activity of said protein kinase,
   (c) identifying the candidate compound as a potential HCV anti-viral agent if the activity determined in step (b) is lower than the activity of said protein kinase determined in the biological system in the absence of the candidate compound, and
   (d) if the candidate compound is identified as a potential HCV anti-viral agent, incubating hepatocytes with the candidate compound, and assessing one or more of HCV entry in the incubated hepatocytes and HCV infection of the incubated hepatocytes.

2. The method according to claim 1, wherein the candidate compound is selected from the group consisting of small molecules, monoclonal antibodies, polyclonal antibodies, RNA polymerase inhibitors, antisense compounds, ribozymes, siRNAs 1 siDNAs, and any combination thereof.

3. The method according to claim 1, wherein the candidate compound belongs to a collection or library of candidate compounds.

4. The method according to claim 1, wherein the biological system is a cell.

* * * * *